US012144921B2

(12) United States Patent
Wroe Neild et al.

(10) Patent No.: US 12,144,921 B2
(45) Date of Patent: Nov. 19, 2024

(54) PORT WITH PIERCING MEANS

(71) Applicant: ConvaTec Limited, Flintshire (GB)

(72) Inventors: Sarah Wroe Neild, Flintshire (GB); Manjunath Penagondla, Flintshire (GB); Natalie Brown, Flintshire (GB); Chandan Rangaiah, Flintshire (GB); Liam Davies, Flintshire (GB)

(73) Assignee: CONVATEC LIMITED, Flintshire (GB)

( * ) Notice: Subject to any disclaimer, the term of this patent is extended or adjusted under 35 U.S.C. 154(b) by 0 days.

(21) Appl. No.: 17/872,530

(22) Filed: Jul. 25, 2022

(65) Prior Publication Data

US 2023/0029369 A1    Jan. 26, 2023

Related U.S. Application Data

(63) Continuation of application No. PCT/GB2022/051941, filed on Jul. 25, 2022.

(30) Foreign Application Priority Data

Jul. 23, 2021 (GB) ..................... 2110650

(51) Int. Cl.
  A61F 15/00      (2006.01)
  A61M 1/00       (2006.01)
  A61F 13/00      (2006.01)
(52) U.S. Cl.
  CPC ............. *A61M 1/90* (2021.05); *A61F 15/00* (2013.01); *A61F 2013/00536* (2013.01)

(58) Field of Classification Search
  CPC .......... A61F 13/00068; A61F 13/00072; A61F 13/0216; A61F 15/00; A61F 2013/00417;
  (Continued)

(56) References Cited

U.S. PATENT DOCUMENTS 11,690,952 B2    7/2023 Kamen et al.
11,690,953 B2    7/2023 Lawrence et al.
(Continued)

FOREIGN PATENT DOCUMENTS

EP    3824925 B1    7/2023
EP    4204040 A1    7/2023
(Continued)

*Primary Examiner* — Catherine L. Anderson
*Assistant Examiner* — Jihad Dakkak
(74) *Attorney, Agent, or Firm* — TAFT STETTINIUS & HOLLISTER LLP; Ryan O. White; Derek B. Lavender

(57) ABSTRACT

A port is provided for use with a wound dressing. The port has piercing means to change the configuration of wound dressing for use in a pressure gradient wound therapy apparatus or for use without a pressure gradient wound therapy apparatus. The port is for connecting a non-atmospheric pressure source to a wound dressing. It comprises a first aperture configured to connect to the non-atmospheric pressure source; and a wound dressing contact surface. The wound dressing contact surface includes a second aperture in fluid communication with the first aperture and configured to allow fluid communication with the wound dressing. The piercing means is configured to pierce the wound dressing as the wound dressing contact surface of the port is applied to the wound dressing.

18 Claims, 9 Drawing Sheets

(58) Field of Classification Search
CPC ........... A61F 2013/00536; A61M 1/90; A61M 1/912; A61M 37/0015
See application file for complete search history.

(56) References Cited

U.S. PATENT DOCUMENTS

| | | | |
|---|---|---|---|
| 11,701,300 B2 | 7/2023 | Lanier, Jr. et al. | |
| 11,702,233 B2 | 7/2023 | Grant et al. | |
| 11,706,876 B2 | 7/2023 | Halac et al. | |
| 11,712,513 B2 | 8/2023 | Gray et al. | |
| 11,712,517 B2 | 8/2023 | Lawrence et al. | |
| 11,717,608 B1 | 8/2023 | Schiff et al. | |
| 11,717,609 B2 | 8/2023 | Kamen et al. | |
| 11,738,139 B2 | 8/2023 | Gray | |
| 11,744,777 B2 | 9/2023 | Bourelle et al. | |
| 11,752,257 B2 | 9/2023 | Hwang et al. | |
| 11,759,564 B2 | 9/2023 | Streit et al. | |
| 11,771,822 B1 | 10/2023 | Imboden | |
| 11,771,824 B2 | 10/2023 | Pizzochero et al. | |
| 11,779,697 B2 | 10/2023 | Shor et al. | |
| 11,786,173 B2 | 10/2023 | Huddleston et al. | |
| 11,786,651 B2 | 10/2023 | Kamen et al. | |
| 11,793,930 B2 | 10/2023 | Chiu et al. | |
| 11,801,340 B2 | 10/2023 | Antonio et al. | |
| 11,813,427 B2 | 11/2023 | Kamen et al. | |
| 11,839,739 B2 | 12/2023 | Skutnik et al. | |
| 11,964,126 B2 | 4/2024 | Lanier, Jr. et al. | |
| 11,969,577 B1 | 4/2024 | Sahani et al. | |
| 11,980,737 B2 | 5/2024 | Streit et al. | |
| 11,980,738 B1 | 5/2024 | Lipman et al. | |
| 11,988,536 B2 | 5/2024 | Searle et al. | |
| 11,992,650 B2 | 5/2024 | Kamen et al. | |
| 11,992,653 B2 | 5/2024 | O'Connor et al. | |
| 12,005,226 B1 | 6/2024 | West et al. | |
| 12,011,569 B2 | 6/2024 | Kapas et al. | |
| 12,012,241 B2 | 6/2024 | Lanigan et al. | |
| 2003/0078610 A1* | 4/2003 | Yedlowski | A61F 13/046 606/179 |
| 2007/0055205 A1* | 3/2007 | Wright | A61F 15/004 424/447 |
| 2010/0228206 A1* | 9/2010 | Larsson | A61M 1/85 604/319 |
| 2014/0163486 A1* | 6/2014 | Riesinger | A61M 1/915 604/319 |
| 2015/0258259 A1* | 9/2015 | Johannison | A61F 13/05 604/319 |
| 2016/0175500 A1* | 6/2016 | Cali | A61M 1/912 604/319 |
| 2016/0206478 A1* | 7/2016 | Nordbo | A61F 13/00085 |
| 2018/0078686 A1 | 3/2018 | Proctor, Jr. et al. | |
| 2018/0104394 A1* | 4/2018 | Locke | A61M 1/966 |
| 2020/0000985 A1 | 1/2020 | Seddon et al. | |
| 2020/0086016 A1* | 3/2020 | Bannister | A61M 1/92 |
| 2020/0100945 A1 | 4/2020 | Albert et al. | |
| 2023/0045643 A1* | 2/2023 | Baeke | A61M 1/91 |
| 2023/0211137 A1 | 7/2023 | Peppi et al. | |
| 2023/0226271 A1 | 7/2023 | Lanigan et al. | |
| 2023/0226273 A1 | 7/2023 | Kamen et al. | |
| 2023/0226274 A1 | 7/2023 | Kamen et al. | |
| 2023/0233758 A1 | 7/2023 | Gregory et al. | |
| 2023/0248904 A1 | 8/2023 | Chiu et al. | |
| 2023/0248920 A1 | 8/2023 | Quinn et al. | |
| 2023/0256160 A1 | 8/2023 | Yodfat et al. | |
| 2023/0270933 A1 | 8/2023 | Sjolund et al. | |
| 2023/0270936 A1 | 8/2023 | Smith et al. | |
| 2023/0277803 A1 | 9/2023 | Horvath et al. | |
| 2023/0285236 A1 | 9/2023 | Liu et al. | |
| 2023/0310761 A1 | 10/2023 | Chowdhury | |
| 2023/0330327 A1 | 10/2023 | Imran | |
| 2023/0330328 A1 | 10/2023 | Moberg et al. | |
| 2023/0347075 A1 | 11/2023 | Nekouzadeh et al. | |
| 2023/0355877 A1 | 11/2023 | Hwang et al. | |
| 2023/0364330 A1 | 11/2023 | Hwang et al. | |
| 2023/0372606 A1 | 11/2023 | Kamen et al. | |
| 2023/0381407 A1 | 11/2023 | Yu et al. | |
| 2023/0381408 A1 | 11/2023 | Streit et al. | |
| 2023/0398288 A1 | 12/2023 | Skutnik et al. | |
| 2023/0414865 A1 | 12/2023 | Zhao et al. | |
| 2024/0139408 A1 | 5/2024 | Estes | |
| 2024/0148964 A1 | 5/2024 | Politis et al. | |
| 2024/0148980 A1 | 5/2024 | Gazeley et al. | |
| 2024/0165388 A1 | 5/2024 | Damiano et al. | |
| 2024/0195058 A1 | 6/2024 | Blumberg, Jr. | |
| 2024/0197984 A1 | 6/2024 | Murphy et al. | |

FOREIGN PATENT DOCUMENTS

| | | | |
|---|---|---|---|
| EP | 2575935 B2 | 8/2023 | |
| EP | 3804786 B1 | 8/2023 | |
| EP | 2908883 B1 | 9/2023 | |
| EP | 3035978 B1 | 9/2023 | |
| EP | 3503942 B1 | 9/2023 | |
| EP | 3769802 B1 | 9/2023 | |
| EP | 2961471 B1 | 10/2023 | |
| EP | 3038672 B1 | 10/2023 | |
| EP | 4262919 A1 | 10/2023 | |
| EP | 3648816 B1 | 4/2024 | |
| EP | 3656417 B1 | 4/2024 | |
| EP | 3799903 B1 | 4/2024 | |
| EP | 4351678 A2 | 4/2024 | |
| EP | 3697479 B1 | 5/2024 | |
| EP | 3733227 B1 | 5/2024 | |
| EP | 4364766 A2 | 5/2024 | |
| EP | 4373552 A1 | 5/2024 | |
| EP | 3570909 B1 | 6/2024 | |
| EP | 3632487 B1 | 6/2024 | |
| EP | 3656699 B1 | 6/2024 | |
| EP | 3700416 B1 | 6/2024 | |
| EP | 3928687 B1 | 6/2024 | |
| EP | 4385551 A2 | 6/2024 | |
| EP | 4389173 A2 | 6/2024 | |
| WO | WO-2013043972 A1 * | 3/2013 | .......... A61M 1/0086 |
| WO | 2023192486 A1 | 10/2023 | |

* cited by examiner

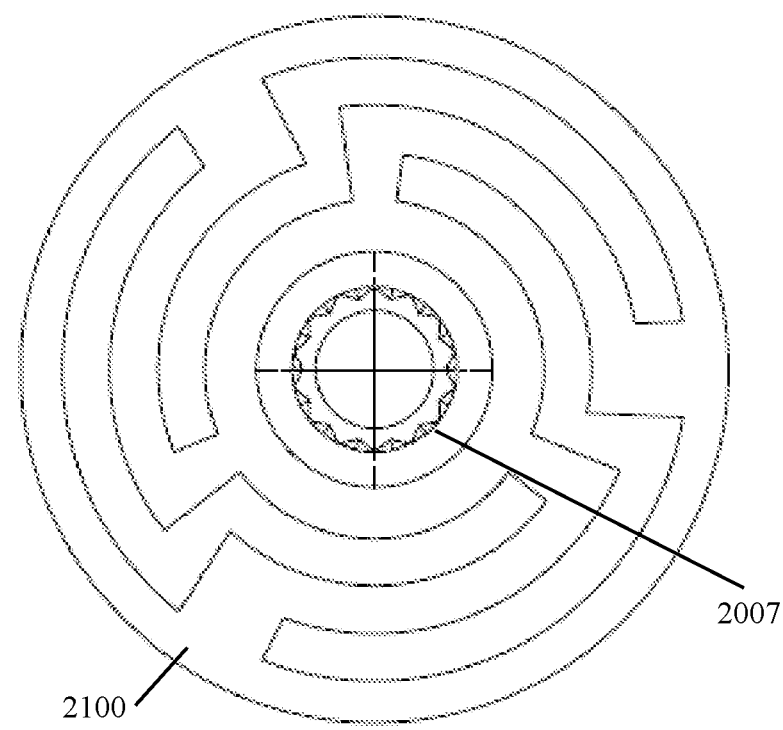
Figure 12c
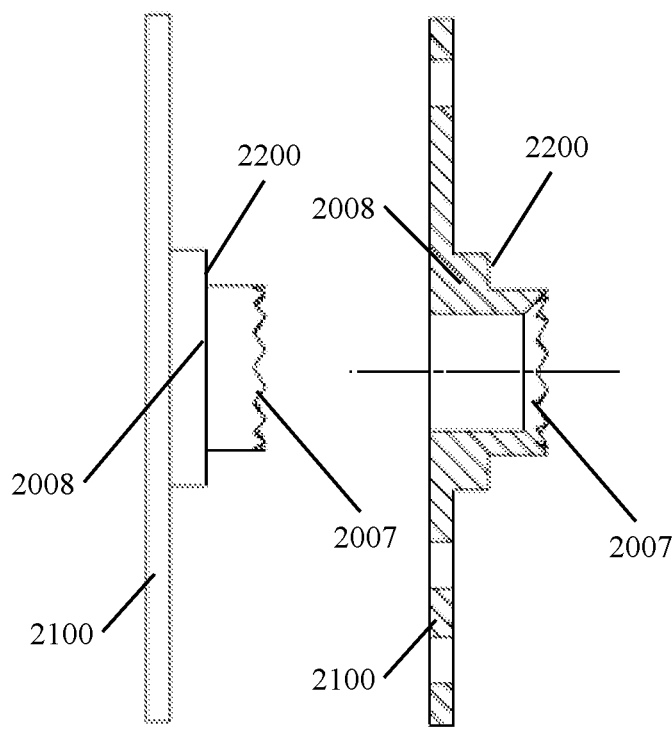
Figure 12d  Figure 12e

PORT WITH PIERCING MEANS

CROSS REFERENCE TO RELATED DISCLOSURES

The present disclosure is a continuation of international application no. PCT/GB2022/051941 filed on Jul. 25, 2022 and claims the benefit of GB2110650.5 filed on Jul. 23, 2021, the contents of which are incorporated herein by reference in entirety.

TECHNICAL FIELD OF THE INVENTION

The present invention relates to a port for use with a wound dressing, in particular to a port with piercing means to change the configuration of wound dressing for use in a pressure gradient wound therapy apparatus or for use without a pressure gradient wound therapy apparatus.

BACKGROUND TO THE INVENTION

Health care professionals (HCPs) are required to evaluate and treat a variety of wounds with different requirements which can change as treatment progresses. Accordingly, HCPs keep stocks of different types of dressings for different requirements.

Pressure gradient wound therapy (positive or negative) is one known way of treating various wound types. Typically, this involves applying a pressure differential between a sealed region of a wound dressing and the surrounding environment to assist with healing the wound, e.g. through removal of oedema, increasing blood flow, mechanical contraction of the wound, increasing formation of granulation tissue and/or active removal of excess exudate from the wound. Wound therapy of this type is particularly effective for the treatment of open traumatic, non-traumatic and chronic wounds.

Amongst different types of dressings are those designed and intended for use as an advanced wound dressing to manage exudate and protect the wound. These can, for example, have a wound contact layer including gelling fibres, such as the Hydrofiber® technology included in Aquacel® surgical dressings available from ConvaTec Ltd of Deeside, UK, which transform into a gel on contact with wound fluid. (Such wound dressings are not intended for use with pressure gradient wound therapy, nor used for such applications in practice, owing to their construction.)

Other types of wound dressing are specially adapted to be used in conjunction with a pressure gradient wound therapy apparatus, e.g. with a negative pressure wound therapy (NPWT pump). In their original incarnation, NWPT systems had large, heavy (not portable/wearable) pump arrangements connected via tubing to the wound; at the wound, a reticulated open cell foam dressing is introduced into the wound and a separate adhesive drape is placed over the top. To connect the tubing to the wound in these large systems, a health care professional pinches the drape and foam beneath, and snips a hole through both drape and foam to form an aperture in the top for connection to the tubing. These systems and the two-part wound dressing (i.e. separate foam and drape) are still widely used in hospitals where professional staff are on-hand to set up to systems.

More recently, and especially in portable or wearable pressure gradient wound therapy systems intended for home-use, one-piece dressings have been introduced, in which an adhesive covering layer and dressing are integrated. An example of such a dressing is the Avelle® dressing available from ConvaTec Limited of Deeside UK. That dressing has a covering film layer with an adhesive border provided around its periphery to form a seal around the wound and a wound contact layer of stitch-bonded Hydrofiber® material. A foam pressure-distribution layer is provided between the covering layer and the wound contact layer (adjacent the covering layer) and additional layers of fenestrated Hydrofiber® layers are provided between the wound contact layer and the pressure-distribution layer. The covering layer is provided with an aperture, to allow connection of tubing from the negative pressure source and in this example, the dressing includes an "airway" extending from the aperture to a connector for connection to tubing through which negative pressure is provided.

Naturally, where a hospital or the like provides both "normal" wound dressings and those for use with pressure gradient wound therapy it needs to keep stocks of both, in various different sizes, which requires space, and lends complexity to the stock-ordering and stock selection process.

The present inventors have identified that it would be beneficial to be able to use a dressing for both pressure gradient wound therapy and "normal" treatment of wounds without a pressure gradient, in order that such treatment could be applied as and when required, and if no longer required, the dressings could still be used.

It is an aim of an embodiment or embodiments of the invention to overcome or at least partially mitigate one or more problems with the prior art and/or to provide an improved wound dressing.

SUMMARY OF THE INVENTION

According to a broad aspect of the invention there is provided a port for connecting a non-atmospheric pressure source to a wound dressing, the port comprising a piercing means.

The port may comprise a first aperture configured to connect to the non-atmospheric pressure source. The port may comprise a wound dressing contact surface. The wound dressing contact surface may comprise a second aperture in fluid communication with the first aperture and configured to allow fluid communication with the wound dressing. The piercing means may be configured to pierce the wound dressing as the wound dressing contact surface of the port is applied to the wound dressing.

According to an aspect of the invention there is provided a port for connecting a non-atmospheric pressure source to a wound dressing, the port comprising: a first aperture configured to connect to the non-atmospheric pressure source; a wound dressing contact surface; the wound dressing contact surface comprising a second aperture in fluid communication with the first aperture and configured to allow fluid communication with the wound dressing; and a piercing means configured to pierce the wound dressing as the wound dressing contact surface of the port is applied to the wound dressing.

Advantageously, providing a port with a piercing means configured to pierce wound dressing (in particular a covering layer of the wound dressing) as the port is applied, can produce an aperture in the wound dressing which makes it possible to change the configuration of a wound dressing. Accordingly, a wound dressing which is normally sealed, e.g. by a closed, sealed and/or uninterrupted cover layer and thereby (only) suitable for use without a pressure gradient wound therapy system can be reconfigured, by introducing an aperture therein so as to configure the wound dressing for use in a pressure gradient wound therapy system (in which non-atmospheric pressure, e.g. negative pressure, can be applied through the aperture).

By allowing the reconfiguration of wound dressings, stock-keeping is simplified. Moreover, if, during "normal" treatment without pressure gradient it is determined that it would be beneficial for pressure gradient wound therapy to be used, such a system could be added, by configuring the wound dressing accordingly, i.e. piercing the dressing with the port to provide an aperture and attaching a source of non-atmospheric pressure (e.g. tubing from a NWPT pump) to the port. Notably, this could be done without the need for an additional dressing change, thus reducing the risk of wound infection. Similarly, if a wound is being treated with a pressure gradient, e.g. NWPT and the amount of exudate produced is reduced, so that NWPT is no longer required, a patient would be able to use up the stock of dressings without the NWPT system, by configuring them for use without the system (i.e. by not attaching the port which forms an aperture in them).

The port may be provided in a kit of parts. The kit may be for use with a selectively configurable wound dressing, the wound dressing being configurable for use in a pressure gradient wound therapy system and without a pressure gradient wound therapy system. The kit may be packaged. The kit may comprise at least one of: a) packaging indicating that the port is configured to pierce a wound dressing (in particular a covering layer thereof) to produce an aperture therein and thereby configure the wound dressing for use in a pressure gradient wound therapy; (b) instructions instructing a user as to how to use the port to configure a wound dressing for use in a pressure gradient wound therapy system; (c) one or more selectively configurable wound dressings, the wound dressings being configurable for use in a pressure gradient wound therapy system and without a pressure gradient wound therapy system; (d) a source of non-atmospheric pressure; or (e) tubing for connection between a wound dressing and a source of non-atmospheric pressure; the kit being arranged within a sealed package.

Providing a port along with one or more other items necessary to understand its function is also advantageous. For example, by including the packaging/instructions of (a) or (b)) a user can understand how to use the port in accordance with the invention; by including the dressings of (c) with which it is to be used, a user has all that is necessary to configure the dressings as desired; and by including one or more of the parts of a pressure gradient wound therapy apparatus (e.g. the source of non-atmospheric pressure (d) or tubing (e), the user will have the parts necessary to set up the apparatus, and reconfigure dressings (which may of course have been obtained separately) for use with the pressure gradient wound therapy apparatus.

When used herein and throughout the specification the term "pressure gradient wound therapy apparatus" is intended to cover a wound therapy apparatus wherein a pressure differential (either positive or negative) is applied between a sealed region of the wound dressing and the surrounding environment.

As used herein, negative pressure wound therapy is a therapeutic technique using a suction dressing to remove excess exudation and promote healing in acute or chronic wounds. A vacuum of −50 to −200 mm Hg, or −75 to −150 mm Hg may be applied with typical negative pressure of −80 to −130 mm Hg, −100 to −130 mm Hg, or often about −125 mm Hg being applied to a wound.

For positive pressure wound therapy, a net positive pressure is applied to the wound, which may include providing simultaneous aspiration and irrigation of the wound. Positive pressure wound therapy may be carried out at a positive pressure of up to 50% atm., typically at a low positive pressure of up to 20% atm., more usually up to 10% atm. at the wound. Positive pressure wound therapy is known and referred to in US20180140755.

Optional features set out below may apply to any aspect of the invention.

The port may be provided in a sterile package. The sealed package in which the kit is arranged may be sterile.

The piercing means may comprise a cutting edge. The piercing means may comprise a blade having a cutting edge. The piercing means may comprise a cutting point. The piercing means may comprise a spike having a cutting point. The piercing means may comprise a plurality of cutting edges or cutting points.

The piercing means may have a curved cutting edge. This may be advantageous in terms of cutting a circular aperture, well suited for attachment to a source of negative pressure.

The piercing means may have a circular cutting edge. This allows a circular aperture to be cut into the wound dressing.

The piercing means may have a part-circular cutting edge. The part circular cutting edge may be at least 180 degrees; at least 240 degrees, or at least 300 degrees of a circle. A part circular cutting edge of such a size can cut a door into the covering layer of the wound dressing. The part circular cutting edge, may, on the other hand, be no more than 180 degrees; no more than 120 degrees or no more than 60 degrees of a circle. A part circular edge of such a size can be twisted to cut a door in the covering layer, or to cut a chad out of the covering layer.

The port may comprise a housing.

The piercing means may extend from the housing. The piercing means may be fixed in position extending from the housing, e.g. a cutting edge or cutting point formed as part of the housing or a blade or spike affixed to the housing, for example by glue or the like.

Alternatively, the piercing means may be configured to extend from the housing, and to be retractable into the housing. The piercing means may be biased towards a retracted position. The bias may be a spring-bias. The piercing means may be spring-loaded. Alternatively, the piercing means may be movable to the retracted position when negative pressure is applied to the first aperture in the port.

Accordingly, a preferred embodiment of the invention provides a port for connecting a non-atmospheric pressure source to a wound dressing, the port comprising: a first aperture configured to connect to the non-atmospheric pressure source; a wound dressing contact surface; the wound dressing contact surface comprising a second aperture in fluid communication with the first aperture and configured to allow fluid communication with the wound dressing; and a piercing means configured to pierce the wound dressing as the wound dressing contact surface of the port is applied to the wound dressing, wherein the piercing means is configured to extend from the housing, and to be retractable into the housing.

The port may comprise an actuator. Actuation of the actuator may move the piercing means to an extended position. The actuator may comprise a button.

The piercing means may be arranged to extend a predetermined extended distance from a base of the port, e.g. from a base of the housing (i.e. to be fixed extending a predetermined extended distance, or to be moveable to a predetermined extended distance in the extended position). This can ensure that the cutting edge or cutting point is able to cut right through a covering layer of a wound dressing, in order that fluid can pass through the aperture cut into the covering layer, whilst not cutting too deeply into the body of the dressing, so as to reduce damage to internal parts of the dressing, such as a pressure distribution layer, or an absorbent layer. For example, where the port is for use in a dressing with a pressure distribution layer sandwiched between a covering layer and an absorbent layer, the cutting edge or cutting point can be arranged to extend through the covering layer, to extend into the pressure distribution layer and not to extend into the absorbent layer.

The predetermined extended distance may be greater than 0.2 mm; greater than 0.5 mm; greater than 1 mm; greater than 1.5 mm; greater than 2 mm; greater than 2.5 mm; greater than 3 mm or greater than 3.5 mm. The predetermined distance may be less than 10 mm; less than 7 mm; less than 5 mm; less than 4 mm; less than 3.5 mm; less than 3 mm; less than 2.5 mm; or less than 1 mm. For example, the predetermined distance may be between 0.5 mm and 2.5 mm, such as between 1 mm and 2 mm, for example about 1.5 mm.

The cutting edge or cutting point may be arranged to retract a predetermined retracted distance into the housing in the retracted position. This can ensure that in the retracted position (to which the cutting edge is preferably biased) it is sufficiently far into the housing as to reduce the likelihood of any accidental injuries. The predetermined retracted distance may be greater than 1 mm; greater than 1.5 mm; greater than 2 mm; greater than 2.5 mm; greater than 3 mm greater than 3.5 mm; greater than 4 mm or greater than 5 mm. The predetermined distance may be less than 15 mm; less than 12 mm; 10 mm; less than 7 mm; less than 5 mm; less than 4 mm; less than 3.5 mm; less than 3 mm; or less than 2.5 mm. For example, the predetermined distance may be between 5 mm and 10 mm, between 6 mm and 9 mm, for example about 7 mm.

Balancing the distance by which the cutting point or cutting edge extends against the distance by which it retracts, can produce a port that is perfectly suited to its purpose.

The wound dressing contact surface may comprise a base. The base may be rigid. The base may be provided with an adhesive underside for connection to the dressing. The base may comprise the second aperture. The piercing means may extend beyond the underside of the base. The piercing means may be arranged to extend through an aperture in the base.

The port may comprise a connector part comprising the first aperture configured to connect to the non-atmospheric pressure source and a base plate comprising the wound dressing contact surface. The connector part and the base plate may be separable. The piercing means may be provided on the connector part. The piercing means on the connector part may be configured to extend through the aperture in the base plate.

The housing may comprise the base. The first aperture may be arranged orthogonal to the second aperture. The base may be annular.

As noted above, the optional features set out above are equally applicable to all aspects (or embodiments) of the invention (including those set out below).

According to an one embodiment of the invention there is provided a packaged kit of parts for use with a selectively configurable wound dressing, the wound dressing being configurable for use in a pressure gradient wound therapy system and without a pressure gradient wound therapy system; the kit comprising: a port comprising a piercing means configured to pierce a covering layer of the wound dressing to produce an aperture therein and thereby configure the wound dressing for use in a pressure gradient wound therapy system; and at least a) packaging indicating that the port is configured to pierce a covering layer of a wound dressing to produce an aperture therein and thereby configure the wound dressing for use in a pressure gradient wound therapy; the kit being arranged within a sealed package.

According to an one embodiment of the invention there is provided a packaged kit of parts for use with a selectively configurable wound dressing, the wound dressing being configurable for use in a pressure gradient wound therapy system and without a pressure gradient wound therapy system; the kit comprising: a port comprising a piercing means configured to pierce a covering layer of the wound dressing to produce an aperture therein and thereby configure the wound dressing for use in a pressure gradient wound therapy system; and at least (b) instructions instructing a user as to how to use the port to configure a wound dressing for use in a pressure gradient wound therapy system; the kit being arranged within a sealed package.

According to an one embodiment of the invention there is provided a packaged kit of parts for use with a selectively configurable wound dressing, the wound dressing being configurable for use in a pressure gradient wound therapy system and without a pressure gradient wound therapy system; the kit comprising: a port comprising a piercing means configured to pierce a covering layer of the wound dressing to produce an aperture therein and thereby configure the wound dressing for use in a pressure gradient wound therapy system; and at least (c) one or more selectively configurable wound dressings, the wound dressings being configurable for use in a pressure gradient wound therapy system and without a pressure gradient wound therapy system; the kit being arranged within a sealed package.

The dressing preferably comprises a covering layer and at least two further layers, a first layer adjacent the covering layer and a second layer separated from the covering layer by the first layer, and the cutting edge is preferably arranged to extend through the covering layer, to extend into the first layer and not to extend into the second layer. For example, a pressure distribution layer may be sandwiched between a covering layer and an absorbent layer, and the cutting edge is preferably arranged to extend through the covering layer, to extend into the pressure distribution layer and not to extend into the absorbent layer. The dressing preferably is a one-piece dressing, wherein the covering layer and at least the first and second layers of the wound dressing are provided as an integral item. The one-piece dressing is preferably provided in a sterile sealed package.

According to an one embodiment of the invention there is provided a packaged kit of parts for use with a selectively configurable wound dressing, the wound dressing being configurable for use in a pressure gradient wound therapy system and without a pressure gradient wound therapy system; the kit comprising: a port comprising a piercing means configured to pierce a covering layer of the wound dressing to produce an aperture therein and thereby configure the wound dressing for use in a pressure gradient wound therapy system; and at least (d) a source of non-atmospheric pressure; the kit being arranged within a sealed package.

According to an one embodiment of the invention there is provided a packaged kit of parts for use with a selectively configurable wound dressing, the wound dressing being configurable for use in a pressure gradient wound therapy system and without a pressure gradient wound therapy system; the kit comprising: a port comprising a piercing means configured to pierce a covering layer of the wound dressing to produce an aperture therein and thereby configure the wound dressing for use in a pressure gradient wound therapy system; and at least (e) tubing for connection between a wound dressing and a source of non-atmospheric pressure; the kit being arranged within a sealed package.

Of course the kit may comprise various combinations of features a to e; for example the kit may comprise at least two features including a+b; the kit may comprise at least two features including a+c; the kit may comprise at least two features including a+d; the kit may comprise at least two features including a+e; the kit may comprise at least two features including b+c; the kit may comprise at least two features including b+d; the kit may comprise at least two features including b+e; the kit may comprise at least two features including c+d; the kit may comprise at least two features including c+e; the kit may comprise at least two features including d+e. The kit may comprise at least three features including a+b+c; the kit may comprise at least three features including a+b+d; the kit may comprise at least three features including a+b+e; the kit may comprise at least three features including a+c+d; the kit may comprise at least three features including a+c+e; the kit may comprise at least three features including a+d+e; the kit may comprise at least three features including b+c+d; the kit may comprise at least three features including b+c+e; the kit may comprise at least three features including b+d+e; or the kit may comprise at least three features including c+d+e. The kit may comprise at least four features including a+b+c+d; the kit may comprise at least four features including a+b+c+e; the kit may comprise at least four features including b+c+d+e. The kit may comprise all five features including a+b+c+d+e.

One particular embodiment includes at least one item selected from a+b; one particular embodiment includes at least one item selected from a+c; one particular embodiment includes at least one item selected from a+d; one particular embodiment includes at least one item selected from a+e; one particular embodiment includes at least one item selected from b+c; one particular embodiment includes at least one item selected from b+d; one particular embodiment includes at least one item selected from b+e; one particular embodiment includes at least one item selected from c+d; one particular embodiment includes at least one item selected from c+e; one particular embodiment includes at least one item selected from d+e; one particular embodiment includes at least one item selected from a+b+c; one particular embodiment includes at least one item selected from a+b+d; one particular embodiment includes at least one item selected from a+b+e; one particular embodiment includes at least one item selected from a+c+d; one particular embodiment includes at least one item selected from a+c+e; one particular embodiment includes at least one item selected from a+d+e; one particular embodiment includes at least one item selected from b+c+d; one particular embodiment includes at least one item selected from b+c+e; one particular embodiment includes at least one item selected from b+d+e; one particular embodiment includes at least one item selected from c+d+e; one particular embodiment includes at least one item selected from a+b+c+d; one particular embodiment includes at least one item selected from a+b+c+e one particular embodiment includes at least one item selected from b+c+d+e.

The packaging may for example be cardboard packaging. The packaging may comprise printed information indicating that the wound dressing is selectively configurable for use in a pressure gradient wound therapy system and without a pressure gradient wound therapy system. The packaging may be sterile; and/or at least part of the packaging, or a sub-package may be sterile.

The instructions instructing a user as to how to configure the wound dressing for use in a pressure gradient wound therapy system and for use without a pressure gradient wound therapy system may be printed on packaging. The instructions instructing a user as to how to configure the wound dressing for use in a pressure gradient wound therapy system and for use without a pressure gradient wound therapy system may be provided on an instruction sheet (which where the kit includes features a+b may be provided in the packaging).

The source of non-atmospheric pressure preferably a source of negative pressure. Alternatively it may be a source of positive pressure. The source of non-atmospheric pressure may be a pump.

The tubing for connection between a wound dressing and a source of non-atmospheric pressure may be transparent tubing. The tubing may be flexible. The tubing may be resilient. The tubing may be formed from a resilient flexible plastics material.

As for the wound dressing:

The wound dressing may comprise a covering layer. The wound dressing may comprise a pressure distribution layer. The covering layer may define a cavity. The pressure distribution layer may be provided in, e.g. contained in, the cavity. The covering layer may comprise an indica; the indica may denote a position (for example a suitable position or the optimal position) in the covering layer to create an aperture to provide fluid communication between the pressure distribution layer and a source of non-atmospheric pressure.

The shape of the indicia may match the shape of the piercing means. The shape of the indicia may match the shape of the cutting edge. The shape of the indicia may match the shape of the housing. The size of the indicia may match the size of the piercing means. The size of the indicia may match the size of the cutting edge. The size of the indicia may match the size of the housing. By matching the shape and/or size of the indicia to the shape and/or size of the piercing means, it is straightforward for the user to align the piercing means with the position denoted by the indicia where the wound dressing should be pierced to cut an aperture therein and thereby configure it for use in a pressure gradient wound therapy system.

In one embodiment the wound dressing may comprise a wound contact layer and a covering layer, the covering layer having a first surface facing the wound contact layer and defining a wound dressing cavity, and a second surface; wherein the second surface of the covering layer comprises an indica, the indica denoting a suitable, or more preferably an optimal, position in the covering layer to create an aperture to provide fluid communication between the wound dressing cavity and a source of non-atmospheric pressure.

In one embodiment the wound dressing may comprise a pressure distribution layer and a covering layer; wherein the covering layer comprises an indica, the indica denoting the optimal position in the covering layer to create an aperture to provide fluid communication between the pressure distribution layer and a source of non-atmospheric pressure.

The indicia may be a mark. The mark may be formed of ink or dye, for example the indicia may be printed. The mark may be formed by discoloration, e.g. the indicia could be laser marked. The indicia may be printed onto the covering layer. Alternatively the indicia could be applied by other means. The covering layer may have an upper side and an underside. The indicia may be applied onto the upper side of the covering layer. The indicia may be applied onto the underside of the covering layer. The covering layer may be transparent or translucent (this would allow indicia to be visible even if printed onto the underside).

The indicia is preferably located out of alignment (i.e. vertical alignment in use) with the centre of the dressing. For example it may be located towards the periphery of the covering layer and/or the pressure distribution layer (or the wound when in use). This assists in the spread of exudate across the full extent of the pressure distribution layer (and across an absorbent layer where an absorbent layer is provided).

The pressure distribution layer may be provided adjacent to the cover layer. The covering layer may define a cavity. The pressure distribution layer may be provided in, e.g. contained in, the cavity. The pressure distribution layer may be gas and liquid permeable and particularly moisture vapour permeable. The pressure distribution layer serves to aid access of exudate to a greater area of the absorbent layer by allowing it to spread under the distribution layer. The pressure distribution layer also serves to even out the negative pressure applied to the wound over the whole dressing (when used for NPWT). The pressure distribution layer is preferably configured to distribute exudate and negative pressure over the dressing. The pressure distribution layer is preferably a foam layer such as a polyester foam of the type XD4200AS manufactured by Caligen or another suitable reticulated foam.

An adhesive layer may be provided so as to form an adhesive border. The adhesive layer may be provided on the underside of the covering layer. The adhesive border may be provided at the periphery of the dressing arranged to adhere the dressing to the skin surrounding the wound to form a fluid tight seal. The adhesive layer may be provided with perforations to assist transport of exudate and fluid through the dressing. The adhesive layer may also be applied to any of the other layers to provide an island configuration.

The indicia may be located in a region of the covering layer within that defined by the adhesive border. For example it may be located towards the periphery of the region of the covering layer inwards of the adhesive border.

In the configuration for use without a pressure gradient wound therapy system the region of the covering layer within that defined by the adhesive border may be closed, sealed and/or uninterrupted, e.g. a continuous unbroken membrane. This restricts/prevents microbes, bacteria or the like from entering the wound dressing and hence from entering the wound. In the configuration for use with a pressure gradient wound therapy system the region of the covering layer within the adhesive border may be interrupted by an opening, the opening being an aperture in the region of the indicia for connection to a source of non-atmospheric pressure. This allows non-atmospheric pressure to be applied to the wound.

The wound dressing may include a dressing body comprising an absorbent material for contacting the wound, i.e. which may be positioned in contact with a wound, in use. The dressing body may be formed from one of more layers. The dressing body may be configured to absorb exudate from the wound, aided by the action of a connected pump assembly. The dressing body may comprise an absorbent foam material, for example a layer of absorbent foam material. The foam material may comprise a superabsorbent material, for example a superabsorbent foam material. The dressing body may be formed of a hydrocolloid material which may gel in the presence of an exudate. The hydrocolloid material may comprise a layer or multiple layers of gelling fibres and absorbent materials. The covering layer may be constructed of a thin film layer (e.g. a polyurethane) enabling moisture vapour to exit the dressing at an increased rate. This combination is particularly suitable for allowing the wound therapy apparatus to manage fluid without the need of a canister. This may be referred to as a "canister-less" or "canister-free" system. In a variant, the wound dressing may be operable to be fluidly connected to a canister into which exudate removed from the wound may be withdrawn. The adhesive border may define an interior region of the wound dressing. The dressing body may be provided in the interior region of the wound dressing.

The wound dressing may comprise a release layer, the release layer being removable to reveal the adhesive border.

The wound dressing may have a thickness between 1 mm to 20 mm, or 2 mm to 10 mm, or 3 mm to 7 mm, for example.

The pressure distribution layer may be a foam layer. The wound dressing may comprise the outer cover layer, the pressure distribution layer, one or more absorbent layer(s) and a silicone gel wound contact layer. The wound dressing may comprise an outer cover layer and one or more absorbent layer(s) in combination with a gel-forming fibre. The gel-forming fibre typically is in direct contact with the wound, and thus no additional wound contact layer is required i.e., a silicone gel wound contact layer does not require a silicone gel layer.

Gel-forming fibres include hygroscopic fibres which upon the uptake of wound exudate become moist slippery or gelatinous. The gel forming fibres can be of the type which retain their structural integrity on absorption of exudate or can be of the type which lose their fibrous form and become an amorphous or structureless gel. The gel forming fibres are preferably sodium carboxymethylcellulose fibres, chemically modified cellulosic fibres, alkyl sulphonate modified cellulosic fibres such as those described in WO2012/061225, pectin fibres, alginate fibres, chitosan fibres, hyaluronic acid fibres, or other polysaccharide fibres or fibres derived from gums. The cellulosic fibres preferably have a degree of substitution of at least 0.05 carboxymethyl groups per glucose unit. The gel forming fibres preferably have an absorbency of at least 2 grams 0.9% saline solution per gram of fibre (as measured by the free swell method).

The gel forming fibres are preferably chemically modified cellulosic fibres in the form of a fabric and in particular carboxymethylated cellulose fibres as described in PCT WO00/01425 to Azko Nobel UK Ltd, and can be provided by a layer of gel forming fibres preferably located in a port of the cover layer or as a layer of fibres in a conduit of the wound dressing. When present in the conduit, the layer of fibres can also serve to keep the conduit open to the passage of fluid in the event that the conduit is kinked or otherwise restricted by being lain on or leaned on by the user. The carboxymethylated cellulosic fabrics preferably have a degree of substitution between 0.12 to 0.35 as measured by IR spectroscopy (as defined in WO00/01425) more preferably a degree of substitution of between 0.20 and 0.30 and are made by carboxymethylating a woven or non-woven cellulosic fabric such that the absorbency is increased. Particular preferred fabrics have an absorbency of between 10 g/g of sodium/calcium chloride as defined above to 30 g/g of sodium/calcium chloride as measured by the method described in BS EN 13726-1 (2002) "Test methods for primary wound dressings", section 3.2 "Free swell absorptive capacity". Particularly preferred fabrics have an absorbency of 15 g/g to 25 g/g and most preferred of 15 g/g to 20 g/g of sodium/calcium chloride as measured by the method defined above.

The cellulosic fabric preferably consists solely of cellulosic fibre but may contain a proportion of non-cellulosic textile fibre or gel forming fibre. The cellulosic fibre is of known kind and may comprise continuous filament yarn and/or staple fibre. The carboxymethylation is generally performed by contacting the fabric with an alkali and a carboxymethylating agent such a chloracetic acid in an aqueous system. The fabric is preferably of a non-woven type to reduce shedding in the wound on cutting the dressing. Preferably the fabric is hydroentangled and thus comprises a series of apertures on a microscopic scale.

Where present, the absorbent layer of the wound dressing is capable of absorbing exudate from the wound and allowing the passage of fluid through it. The absorbent layer can comprise any absorbent capable of absorbing exudate while allowing the passage of fluid through it, such as a foam, sponge or fibre-based material, preferably the absorbent layer is provided by gel forming fibres of the same type or of a different type as those discussed above. The gel-forming fibres are hygroscopic fibres which upon the uptake of wound exudate become moist slippery or gelatinous and thus reduce the tendency for the surrounding fibres to adhere to the wound. The gel forming fibres are preferably spun sodium carboxymethylcellulose fibres, chemically modified cellulosic fibres, alkyl sulphonate modified cellulosic fibres such as those described in WO2012/061225, pectin fibres, alginate fibres, chitosan fibres, hyaluronic acid fibres, or other polysaccharide fibres or fibres derived from gums. The cellulosic fibres preferably have a degree of substitution of at least 0.05 carboxymethyl groups per glucose unit and more preferably are lightly substituted so that the absorbency of the fibres is limited. The gel forming fibres preferably have an absorbency of at least 2 grams 0.9% saline solution per gram of fibre (as measured by the method described above) but less than 30 grams 0.9% saline solution per gram of fibre. The gel forming fibres are preferably carboxymethylated cellulose fibres as described in PCT WO00/01425 to Azko Nobel UK Ltd which describes lightly carboxymethylated cellulose fabrics. The gel forming fibres are preferably lightly carboxymethylated in order to reduce the tendency of the absorbent layer to gel block and block the pathway for fluid from the wound, e.g. through the absorbent layer, the port and to a distal end of the conduit.

Preferably an absorbent layer is provided with fenestrations to aid the application of negative pressure to the wound and maintain the pathway for fluid from the wound, through the absorbent layer. Typically, however, fenestrations are only provided in internal absorbent layers.

Although the absorbent layer can be in direct contact with the wound, preferably the dressing comprises a wound contact layer, positioned between the wound and the absorbent layer(s). The wound contact layer may be capable of absorbing exudate from the wound and transmitting it to the absorbent layer. Thus, there may be provided "internal" absorbent layers as defined above, preferably including fenestrations and an external absorbent layer, which forms the wound contact layer. Like the internal absorbent layer, the wound contact layer may be capable of allowing the passage of fluid through it so that pressure (either positive or negative) may applied to the wound and the pathway for fluid/exudate from the wound to the distal end of the conduit may be maintained.

The wound contact layer may include gel-forming fibres (e.g. of the type discussed herein), or a silicone gel, for example.

Preferably the wound contact layer comprises gel-forming fibres. The gel-forming fibres may be the same or a similar type to those comprising the absorbent layer but the wound contact layer may be strengthened to increase its integrity and that of the dressing. For example, the wound contact layer may be of the type described in EP 1904011 and comprise gel-forming fibres in the form of a mat with lines of longitudinal stitching made of cellulose or nylon or polyolefin yarn to increase the integrity of the layer. Preferably the wound contact layer is porous to maintain the pathway for fluid/exudate from the wound to the distal end of the conduit.

Preferably the one or more absorbent layer(s) comprise an internal absorbent layer provided with fenestrations to aid the application of negative pressure to the wound and maintain the pathway for fluid from the wound, through the internal absorbent layer and a wound contact layer comprising gel-forming fibres is also provided.

The (outer) cover layer of the dressing is provided as a bacterial and viral barrier layer which preferably resists the ingress of liquid and air but allows moisture vapour transmission. In this way the cover layer enhances the overall fluid handling capacity of the dressing by allowing for the escape of moisture vapour through the cover while enabling the application of pressure (either positive or negative) to the wound. The outer cover layer is for instance a layer having a MVTR of at least 10,000 g m$^{-2}$ per 24 hours or in the range of from 10,000 gm$^{-2}$ to 50,000 g m$^{-2}$ per 24 hours measured by the method described in BS EN 13726-2 2002 "Test methods for primary wound dressings Part 2 Moisture vapour transmission rate of permeable film dressings". The cover layer may be in the form of a film of polyurethane, for example Epurex 912 T/129 manufactured by Covestro or Inspire 2350 manufactured by Coveris or Medifilm 426 manufactured by Mylan.

The wound dressing preferably is a one-piece dressing. That is to say, it is the covering layer and the body of the wound dressing are provided as an integral item, preferably including an adhesive layer and preferably including a removable release layer. The body of the wound dressing that is provided, along with the covering layer, as an integral item may comprise the pressure distribution layer.

The one-piece dressing may be provided in a package. The package may be a sterile package.

According to another aspect of the invention there is provided a pressure gradient wound therapy apparatus, comprising the kit of any preceding aspect of the invention.

In embodiments, the wound therapy apparatus comprises a negative pressure wound therapy apparatus. In other embodiments, the wound therapy apparatus comprises a positive pressure wound therapy apparatus.

In embodiments, the apparatus may comprise a canister and the wound dressing may be fluidly connected to the canister into which exudate removed from the wound may be withdrawn. In preferred embodiments, the wound dressing may be formed of a hydrocolloid material which may gel in the presence of an exudate and the apparatus may include no cannister. This may be referred to as a "canister-less" system.

The pump assembly may be fluidly connected to an interior region of the wound dressing, for introducing and/or removing gas from within the wound dressing to control the pressure therein.

According to a further broad aspect of the invention there is provided a method of configuring a selectively configurable wound dressing, the wound dressing being configurable for use in a pressure gradient wound therapy system and without a pressure gradient wound therapy system; the method comprising configuring the wound dressing for use with a pressure gradient wound therapy system by cutting an aperture in the wound dressing.

According to an aspect of the invention there is provided a method of configuring a selectively configurable wound dressing, the wound dressing comprising a covering layer and being configurable for use in a pressure gradient wound therapy system and without a pressure gradient wound therapy system; the method comprising configuring the wound dressing for use with a pressure gradient wound therapy system by cutting an aperture in the covering layer of the wound dressing using a port comprising piercing means.

Of course, the port of the method aspects may be the port of the aspects of invention set out above.

And again, of course the wound dressing of the method may comprise any optional feature described above.

For example, the wound dressing may comprise a covering layer, which comprises an indica denoting an optimal position in the covering layer to create an aperture to provide fluid communication between the dressing (e.g. a pressure distribution layer thereof) and a source of non-atmospheric pressure; the method comprising configuring the wound dressing for use with a pressure gradient wound therapy system by cutting an aperture in the covering layer of the wound dressing in the region of the indicia.

Likewise, the wound dressing may comprise a pressure distribution layer, in which case the method may comprise not cutting into the pressure distribution layer, or cutting into but not cutting through the pressure distribution layer. Similarly, the wound dressing may comprise a wound contact layer and the method may comprise not cutting into the wound contact layer, or cutting into, but not cutting through the wound contact layer. The wound dressing may comprise a pressure distribution layer and a wound contact layer and the method may comprise cutting through the covering layer, cutting into, but not through, the pressure distribution layer, and not cutting into the wound contact layer.

The wound dressing may comprise a release layer and the method may comprise cutting the aperture, then removing the release layer, then applying the dressing to a wound.

The method may comprise applying the port to cut the aperture, then removing a chad cut from the aperture before attaching the port.

The method may comprise simultaneously applying the port to cut the aperture and attaching the port to the wound dressing. The method may comprise cutting an aperture so as to form a hanging chad or door at the edge of the opening.

The method may be a method of re-purposing a wound dressing that is provided on a wound and configured for use without a pressure gradient wound therapy system; the method comprising cutting an aperture in the wound dressing (in-situ) using the piercing means of the port in order to configure the wound dressing for use with a pressure gradient wound therapy system.

The method may comprise attaching a non-atmospheric pressure source to the wound dressing after configuring the wound dressing for use with a pressure gradient wound therapy system.

DETAILED DESCRIPTION OF THE INVENTION

In order that the invention may be more clearly understood one or more embodiments thereof will now be described, by way of example only, with reference to the accompanying drawings, of which:

FIG. 7b is a cross section through the port of FIG. 7a;

FIG. 12b is a lateral cross section through the port of FIG. 12a;

FIG. 12c is a plan view of an integrated piercing means and biasing means of the port of FIG. 12a FIG. 12d is a side view of the integrated piercing means and biasing means of FIG. 12c; and FIG. 12e is a lateral cross section through the integrated piercing means and biasing means of FIG. 12c.

Figure 1:
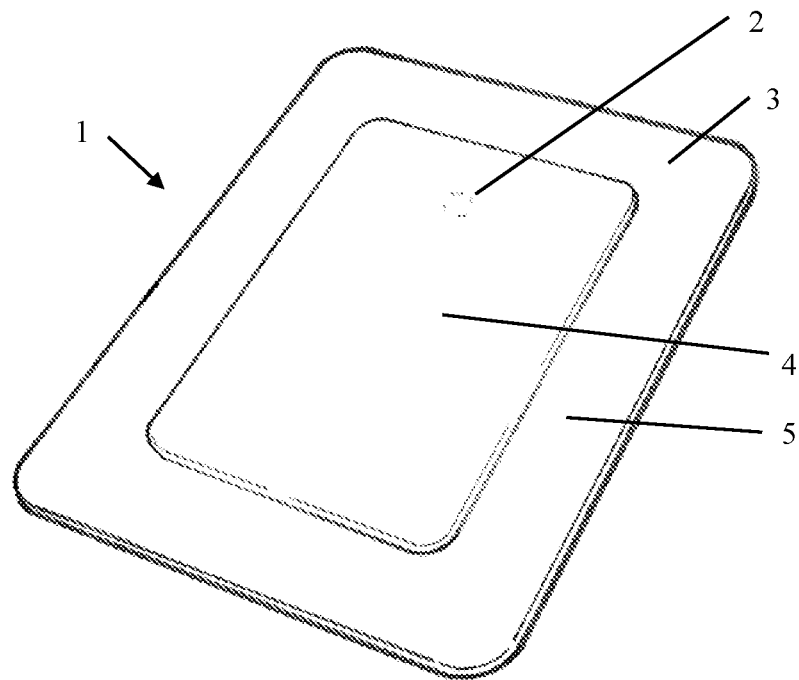
FIG. 1 is a schematic representation of an embodiment of a wound dressing configured for use without a wound therapy apparatus.

Embodiments disclosed herein relate to apparatus and methods of treating a wound both with and without reduced or positive pressure (typically negative pressure). Some embodiments including pump and wound dressing component. The wound dressings discussed are "one-piece" dressings incorporating both a covering layer and an absorbent body.

As disclosed herein the present invention may comprise a port; or a kit comprising the port and other apparatus for providing pressure gradient wound therapy to a wound.

As used herein the expression "wound" may include an injury to living tissue may be caused by a cut, blow, or other impact, typically one in which the skin is cut or broken. A wound may be a chronic or acute injury. Acute wounds occur as a result of surgery or trauma. They move through the stages of healing within a predicted timeframe. Chronic wounds typically begin as acute wounds. The acute wound can become a chronic wound when it does not follow the healing stages resulting in a lengthened recovery. It is believed that the transition from acute to chronic wound can be due to a patient being immuno compromised.

Chronic wounds may include for example: venous ulcers (such as those that occur in the legs), which account for the majority of chronic wounds and mostly affect the elderly, diabetic ulcers (for example, foot or ankle ulcers), peripheral arterial disease, pressure ulcers, or epidermolysis bullosa (EB).

Examples of other wounds include, but are not limited to, abdominal wounds or other large or incisional wounds (either as a result of surgery, trauma, stemiotomies, fasciotomies, or other conditions), dehisced wounds, acute wounds, chronic wounds, subacute and dehisced wounds, traumatic wounds (such as from orthopaedic trauma), flaps and skin grafts, lacerations, abrasions, contusions, burns, diabetic ulcers, pressure ulcers, stoma, surgical wounds, trauma and venous ulcers, broken bones or the like.

Wounds may also include a deep tissue injury. Deep tissue injury is a term proposed by the National Pressure Ulcer Advisory Panel (NPUAP) to describe a unique form of pressure ulcers. These ulcers have been described by clinicians for many years with terms such as purple pressure ulcers, ulcers that are likely to deteriorate and bruises on bony prominences.

The technology disclosed can be used on an acute or chronic wound.

Wounds are believed to be more susceptible to infection under the following circumstances. If the wounds are chronic wounds, or if an object which caused the wound was dirty or contained bacteria, or from a bite, or contains remnant or a whole object that caused the wound, or a wound that is large or deep, or jagged edges to the wound, or elderly, or chronic because by their nature a wound site is open; and/or if the patient has: diabetes type 1 or type 2, is elderly, or has a compromised immune system.

Pressure gradient wound therapy may also be useful for treating second- and third-degree burns, as well as being useful for laparotomy surgery i.e., a large incision through an abdominal wall to gain access into the abdominal cavity.

Figure 2:
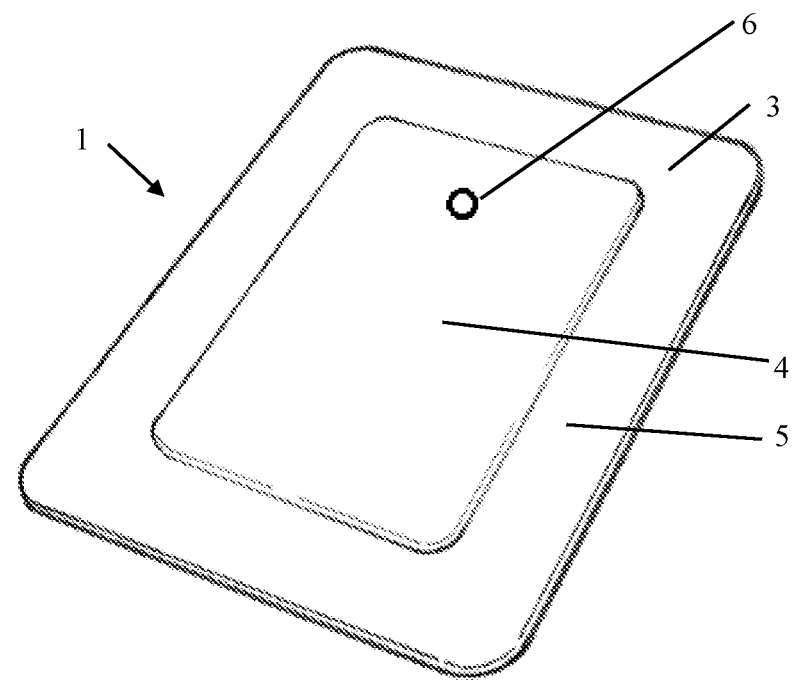
FIG. 2 is a schematic representation of the wound dressing of FIG. 1 configured for use with a wound therapy apparatus.

FIGS. 1 and 2 illustrates an embodiment of a wound dressing 1 for use in accordance with the invention in two different configurations.

In general, the invention relates to the port 20/200/2000 (of FIGS. 7a to 7c, FIGS. 8a and 8b and FIGS. 12a to 12e) which is used in configuration of a wound dressing 1, the wound dressing 1 being selectively configurable for use without a pressure gradient wound therapy system or for use with a pressure gradient wound therapy system, e.g. negative pressure wound therapy.

As shown in FIG. 1, the wound dressing 1 includes an optional indicia 2 visible on the upper (outside) surface of a covering layer 3 of the dressing 1. The covering layer 3 has a raised central region 4, where it overlies a dressing body, which can include a pressure dispersion layer; an absorbent/superabsorbent layer/layers; and a wound-contact layer. The dressing 1 also has a border region 5, where it overlies an adhesive layer. A removable release layer (not shown) is provided on the underside.

The indicia 2 is a marking which indicates where the dressing should be cut to form an aperture in order to configure the dressing for use with a pressure gradient wound therapy system; the dressing being configured for use without a pressure gradient wound therapy system unless/until an aperture is cut in the covering layer. In this embodiment, the indicia 2 is shown as a circle formed in dashed lines, arranged in the optimal position for connection of a source of non-atmospheric pressure. Obviously in other embodiments alternative shapes/signs could be used and of course the indicia need not be in dashed lines.

Moreover it is contemplated that the port 20/200/2000 may be used with dressings not having an indicia at all, with the user following instructions, in order to pierce the covering layer in a suitable location (e.g. the region shown by reference numeral 2).

As illustrated in FIG. 1, the wound dressing 1 is configured for use without a pressure gradient wound therapy system. To use the wound dressing 1 without a pressure gradient wound therapy system, the release layer is simply removed and the dressing applied in the same way as an ordinary wound dressing. It will be noted that the entire raised central region 4 of the covering layer 3 is a continuous unbroken membrane, uninterrupted and closed, so that the wound (within the region defined by the adhesive border) is in a sealed environment, restricting/preventing bacteria/microbes entering the wound and causing infection.

FIG. 2 shows the wound dressing 1 of FIG. 1 configured for use with a pressure gradient wound therapy system. Here, a user has cut through the cover layer 3 using the port 20 in the region of the indicia 2, to form an aperture 6 in the wound dressing 1 (so that the central region 4 is no longer closed/uninterrupted). With the wound dressing 1 now configured for use with a pressure gradient therapy system, a source of non-atmospheric, e.g. negative, pressure can be connected to the aperture 6 via the port 20/200/2000 to aid the wound-healing process.

For example, the port 20/200/2000 can be adhered to the wound dressing 1, such that a conduit through the port is aligned with the aperture 6; the port can be connected via tubing (not shown in FIGS. 1 and 2) to a pump (also not shown in FIGS. 1 and 2) producing negative pressure.

Figure 7A:
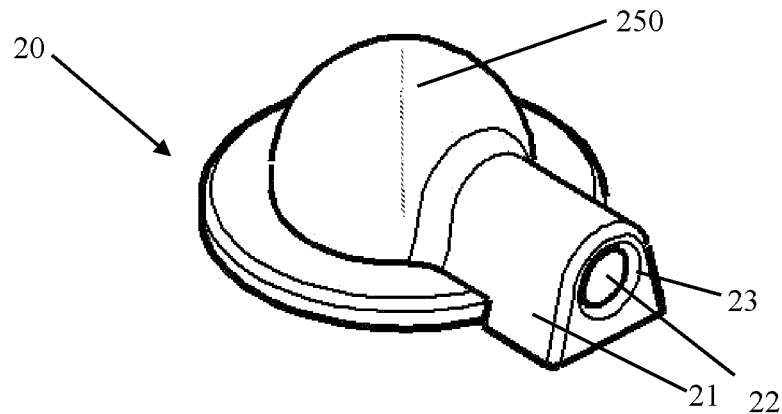
FIG. 7a is a cross section through a port.
Figure 7B:
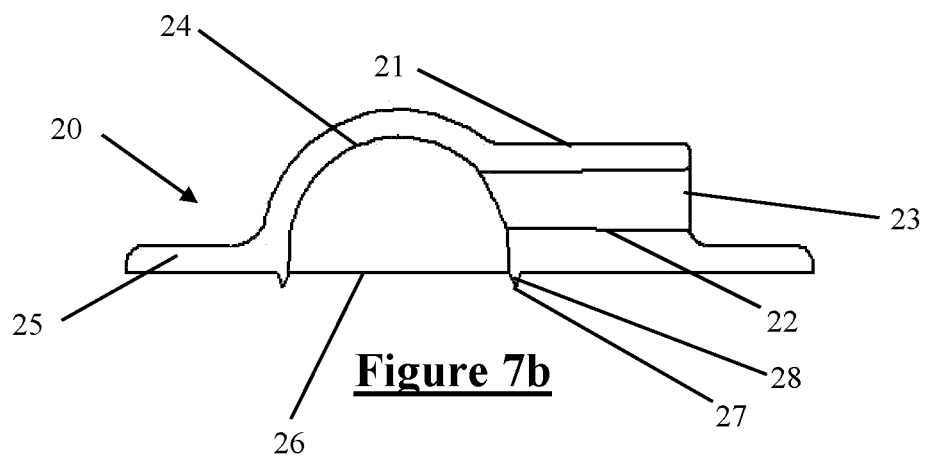
Figure 11:
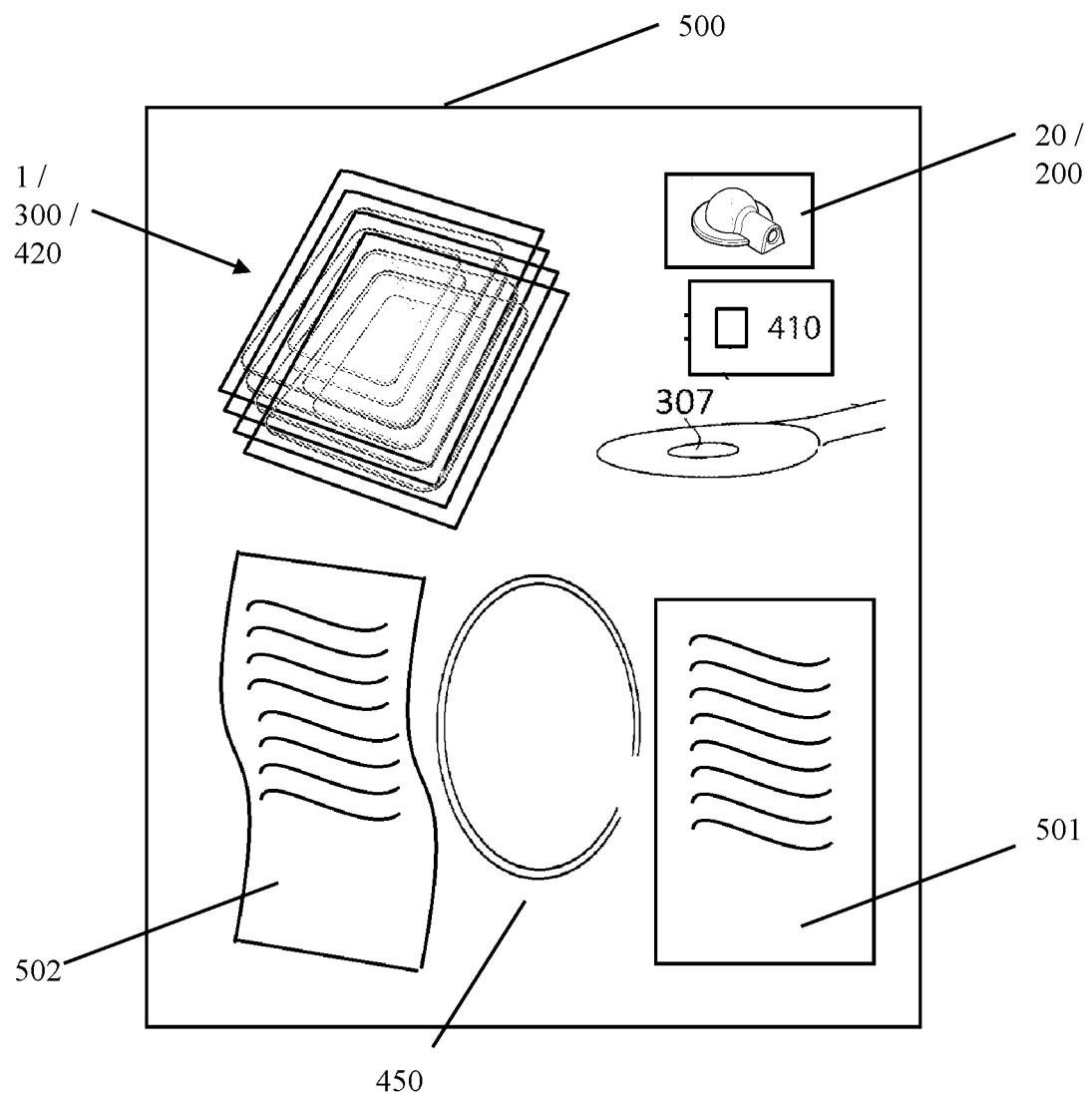
FIG. 11 is a schematic representation of a kit of parts
Figure 12A:
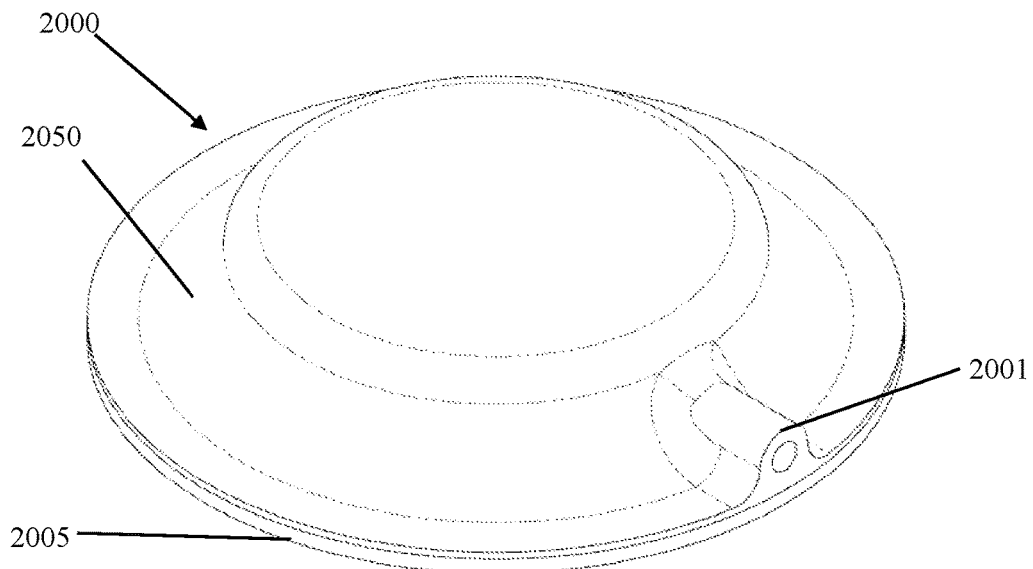
FIG. 12a is an isometric view of another embodiment of a port.
Figure 12B:
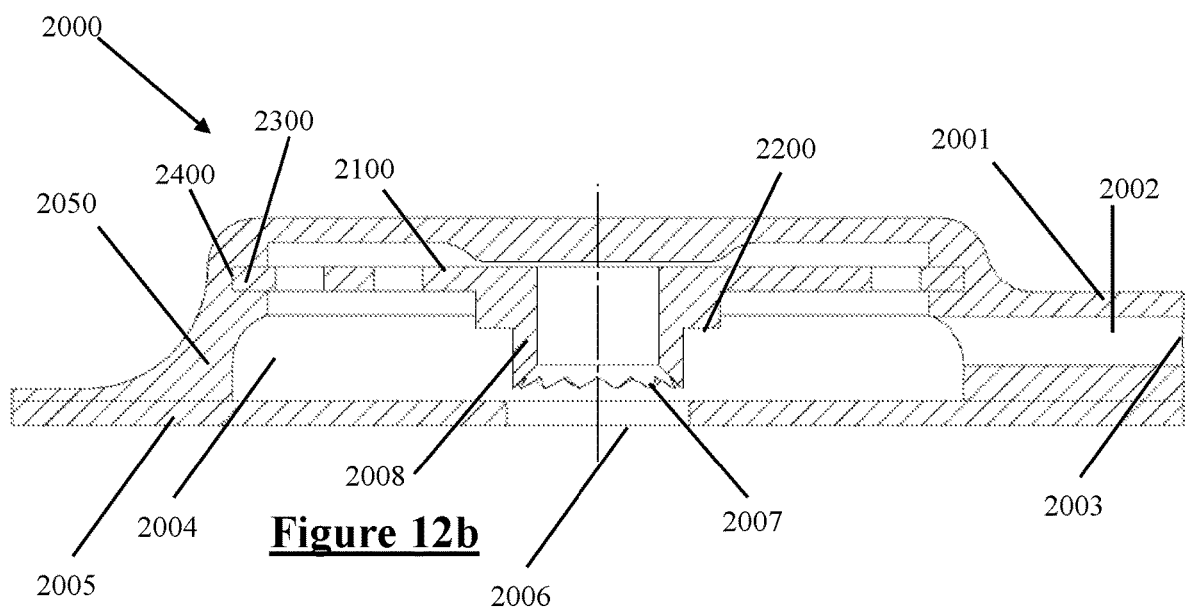

A first embodiment of a port 20 best seen in FIGS. 7a and 7b is specially configured, not only to carry out its primary function associated with prior art ports (i.e. to connect the wound dressing to a source of negative pressure), but also to pierce the covering layer of a wound dressing, whilst not cutting too deeply into the dressing. The port 20 may be provided in a sterile package and as part of a kit, as discussed in more detail below, with reference to FIG. 11.

Focusing initially on the primary and standard function of the port, 20, the port 20 (that of connecting a non-atmospheric pressure source to a wound dressing), the port 20 can be seen to include a generally tubular connector part 21 with a conduit 22 extending from a first aperture 23 configured to connect to a non-atmospheric pressure source, in the form of tubing. The connection being made by a simple push-fit of the tubing into the aperture, so that it is held in a resistance fit in the conduit 22.

The conduit in this example opens into the side of a hemi-spherical chamber 24 provided in the underside of a dome 250. Extending outwardly from the base of the dome 250 is an annular base plate 25. The underside of the base plate 25 and the base of the dome provides a wound dressing contact surface at the base of the port 20. The base plate 25 and dome 250 together form a housing. The base of the hemispherical chamber is open, and as such defines a second aperture 26, which is provided in the wound dressing contact surface and is in fluid communication with the first aperture via the hemispherical chamber 24 and conduit 22. As such the port is configured to allow fluid communication with the wound dressing via the first aperture 23 and second aperture 26, which is orthogonal thereto. Of course, various alternative shapes and sizes of port may be determined by those skilled in the art.

The port 20 of this embodiment also includes a piercing means configured to pierce the cover layer of a wound dressing as the wound dressing contact surface of the port 20 is applied to the wound dressing. In this embodiment, the piercing means is quite straightforward and takes the form of a cutting edge 27 formed integrally with the port, at the end of a downwardly depending annular projection 28 arranged around the aperture 26.

The piercing means of this embodiment is intended to cut a circular aperture, and therefore has a curved cutting edge 27, which defines a circle (to allow a circular aperture to be cut into the wound dressing, to match the shape the aperture 26).

Alternatively, the cutting edge 27 could be provided on a blade (not shown) which could be attached to the base plate of the port in the same location as the cutting edge 27 on the annular projection 28. This would allow for use of different materials, so that a material more suitable for the cutting edge, such as metal could be chosen, whilst a material more suitable for the port, e.g. plastics, in particular a relatively soft resilient plastic, could be chosen for the remainder of the port 20.

It is important that this predetermined extended distance by which the cutting edge 27 extends from the underside of the base plate 25 is carefully controlled, so as to control how far into the wound dressing the cutting edge 27 extends.

In particular, it can be provided that the cutting edge 27 cuts right through the covering layer 3 of a wound dressing, but not into any layer beneath. Alternatively, for example, where the port 20 is for use in a dressing with a pressure distribution layer sandwiched between a covering layer and an absorbent layer (as discussed below with reference to FIGS. 3-6), the cutting edge 27 can be arranged to extend through the covering layer 310, to extend into the pressure distribution layer 340 and not to extend into the absorbent layer(s) 350 (or the wound contact layer 330).

This means that fluid can pass through the aperture cut into the covering layer, whilst not cutting too deeply into the body of the dressing, so as to reduce damage to internal parts of the dressing, such as a pressure distribution layer, or an absorbent layer.

As an example, the predetermined extended distance may be greater than 0.2 mm; greater than 0.5 mm; greater than 1 mm; greater than 1.5 mm; greater than 2 mm; greater than 2.5 mm; greater than 3 mm or greater than 3.5 mm. The predetermined distance may be less than 10 mm; less than 7 mm; less than 5 mm; less than 4 mm; less than 3.5 mm; less than 3 mm; less than 2.5 mm; or less than 1 mm. For example, the predetermined distance may be between 0.5 mm and 2.5 mm, such as between 1 mm and 2 mm, for example about 1.5 mm.

If the cutting edge is sharp enough, it can be simply pushed onto the wound dressing to cut the aperture 6 as shown in FIG. 2. The "chad" can then be removed, and the port 20 subsequently adhered around the aperture 6 in the wound dressing. Alternatively, to improve cutting, the port 20 could be twisted before adhering it to the wound dressing.

The possibility of twisting the port to cut the aperture means that a circular cutting edge is not necessary, a blade only defining part of a circle could be used to cut a circular aperture, or the cutting edge could even be replaced with a cutting point, on the end of a spike, to perforate the cover layer and thereby form one or more apertures, to be arranged in communication with the aperture 26 in the underside of the port. It is considered that it may not always be necessary to remove the chad when cutting the aperture. As such, and as outlined above, apertures could be provided by piercing with a spike, similarly, a non-circular, or even non-curved blade could be provided on the port to cut an aperture in the form of a slit.

It will be understood from the above, that as the port 20 is applied to the dressing it cuts an aperture therein. The aperture may be cut at the same time as the port is attached, e.g. as it is adhered to the wound dressing. Obviously in that case, the step of removal of a chad by would be impossible, but it could simply be sucked out by a source of negative pressure.

Figure 3:
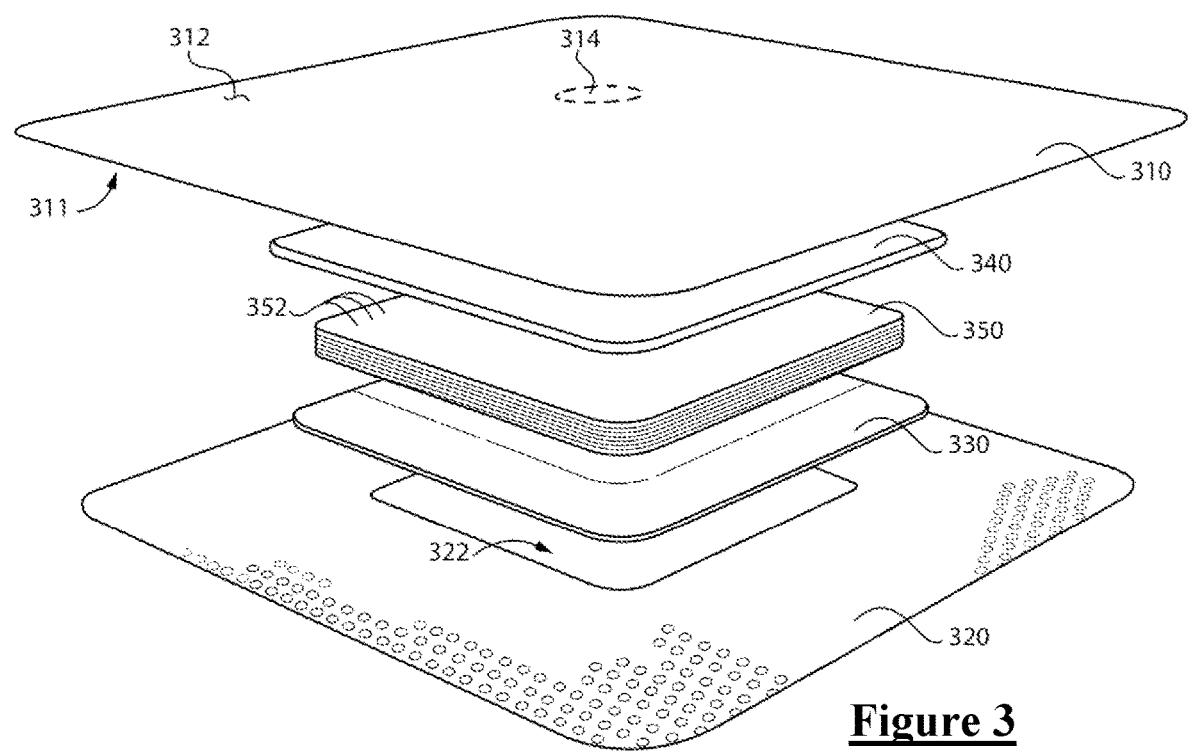
FIG. 3 is an exploded view of another embodiment of a wound dressing configured for use without a wound therapy apparatus.
Figure 4:
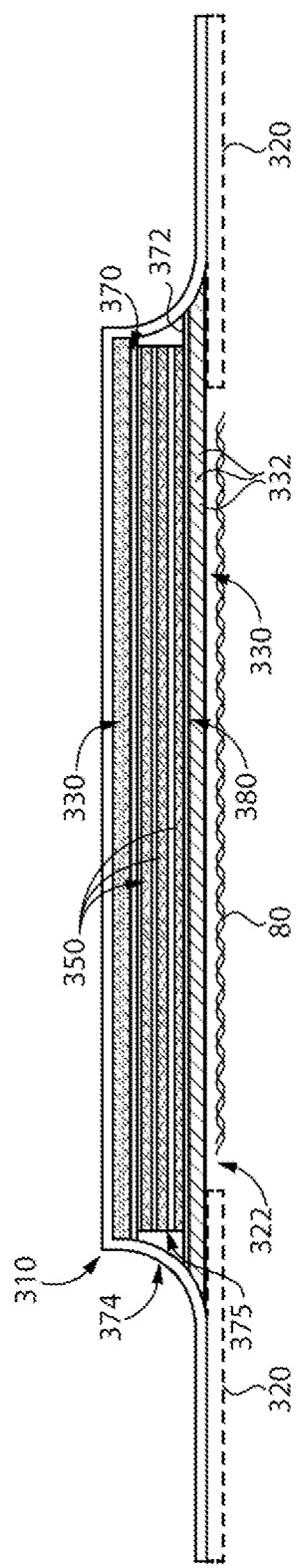
FIG. 4 is a cross-sectional view of the wound dressing illustrated in FIG. 3.

With additional reference to FIGS. 3-4, illustrated therein is a schematic of another exemplary wound dressing 300 that can be selectively configured for use in a pressure gradient wound treatment system, using the port 20.

The illustrated wound dressing 300 generally includes a covering layer 310 and an adhesive layer 320 for adhering the wound dressing 300 adjacent the wound. In certain embodiments, the wound dressing 300 further comprises a wound contact layer 330 for contacting the wound, a pressure dispersion layer 340, a plurality of absorbent material layers 350 disposed between the wound contact layer 330 and the pressure dispersion layer 340.

The covering layer 310 has a first surface 311 and a second surface 312, and the first surface 311 is adjacent, and in contact with, the pressure dispersion layer 340 and the adhesive layer 320. The covering layer 310 defines a cavity in which the pressure dispersion layer 340 is arranged. In certain embodiments, the covering layer 310 is formed of a polyurethane film. The covering layer 310 comprises optional indicia 314 in the form of a dashed circle, arranged in the optimal position for connection to a source of negative pressure.

The polyurethane film is transparent, so the indicia can be printed on the inside first surface 311 or the outside, second, surface 312 of the film layer 310.

The adhesive layer 320 generally defines a border about an opening 322 for receiving the wound. In certain embodiments, the adhesive layer 320 comprises a silicone adhesive. In certain embodiments, the adhesive layer 320 may be perforated.

The wound contact layer 330 overlaps the border defined by the adhesive layer 320, and is configured to contact the wound via the opening 322. In certain embodiments, the wound contact layer 330 may comprise Medicel™. In certain embodiments, the wound contact layer 330 comprises carboxymethylated cellulose fibers. In certain embodiments, the wound contact layer 330 may comprise HYDROFIBER®. In certain embodiments, the wound contact layer 330 may be reinforced, for example via nylon stitching. Thus, the wound contact layer 330 may comprise reinforcing nylon stitching 332.

The pressure dispersion layer 340 is adjacent and in contact with the first surface 311 of the cover layer 310. In certain embodiments, the pressure dispersion layer 340 may be provided as a polyester foam layer. In certain embodiments, the pressure dispersion layer 340 comprises reticulated foam.

The absorbent material layers 350 are positioned between the wound contact layer 330 and the pressure dispersion layer 340. The wound dressing 300 may, for example, comprise eight absorbent material layers 350. In certain embodiments, one or more of the absorbent material layers 350 may comprise carboxymethylated cellulose fibers. In certain embodiments, one or more of the absorbent material layers 350 may comprise Medicel™. In certain embodiments, one or more of the absorbent material layers 350 may comprise HYDROFIBER®. In certain embodiments, one or more of the absorbent material layers 350 further comprises fenestrations 352.

Figure 5:
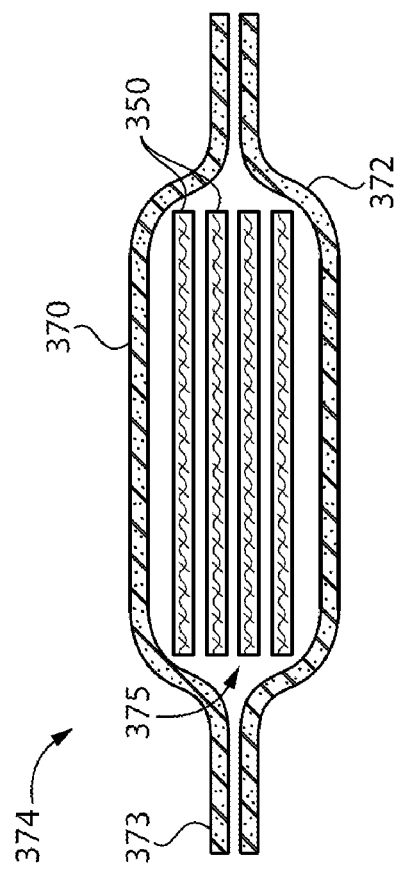
FIG. 5 is a cross sectional view of a portion of the wound dressing illustrated in FIG. 3.

In certain embodiments, as shown in FIG. 4, the wound dressing 300 may include an additional layer 370 between the pressure dispersion layer 330 and the uppermost absorbent layer 350. The additional layer 370 may, for example, be formed of thermoplastic. In certain embodiments, the additional layer 370 may be provided as a thermoplastic spun lace layer. In certain embodiments, the wound dressing 300 may further comprise a nonwoven spun lace layer 372 connected to the wound contact layer 330. In certain embodiments, an envelope structure 374 is formed by joining peripheral portions 373 of the thermoplastic spun lace layer 370 and the nonwoven spun lace layer 372 such that the plurality of absorbent material layers 350 are disposed substantially within an interior cavity 375 of the envelope structure 374, for example as illustrated in FIG. 5. In certain embodiments, the absorbent material layers 350 are disposed within the interior cavity 375 of the envelope structure 374.

In certain embodiments, the wound dressing 300 may include a further layer 380 positioned between the wound contact layer 330 and the lowermost absorbent layer 350. The further layer 380 may, for example, be a polyester/viscose layer.

As is well known, and therefore not shown, the wound dressing 300 may be provided with a removable release layer on the underside, covering the adhesive layer 320 and the underside of the wound contact layer 330; and it may be individually packaged within a sterile package.

As illustrated in FIGS. 3-5, the wound dressing is configured for use without a pressure gradient wound therapy system. To use the wound dressing 300 without a pressure gradient wound therapy system, it is simply removed from its sterile packaging, then the release layer is simply removed and the dressing applied in the same way as an ordinary wound dressing. Again, it will be noted that in this configuration the entire region of the covering layer 310 within the peripheral adhesive border defined by the layer 320 is uninterrupted and closed, sealing the wound against microbes/bacteria that could cause infection.

Figure 6:
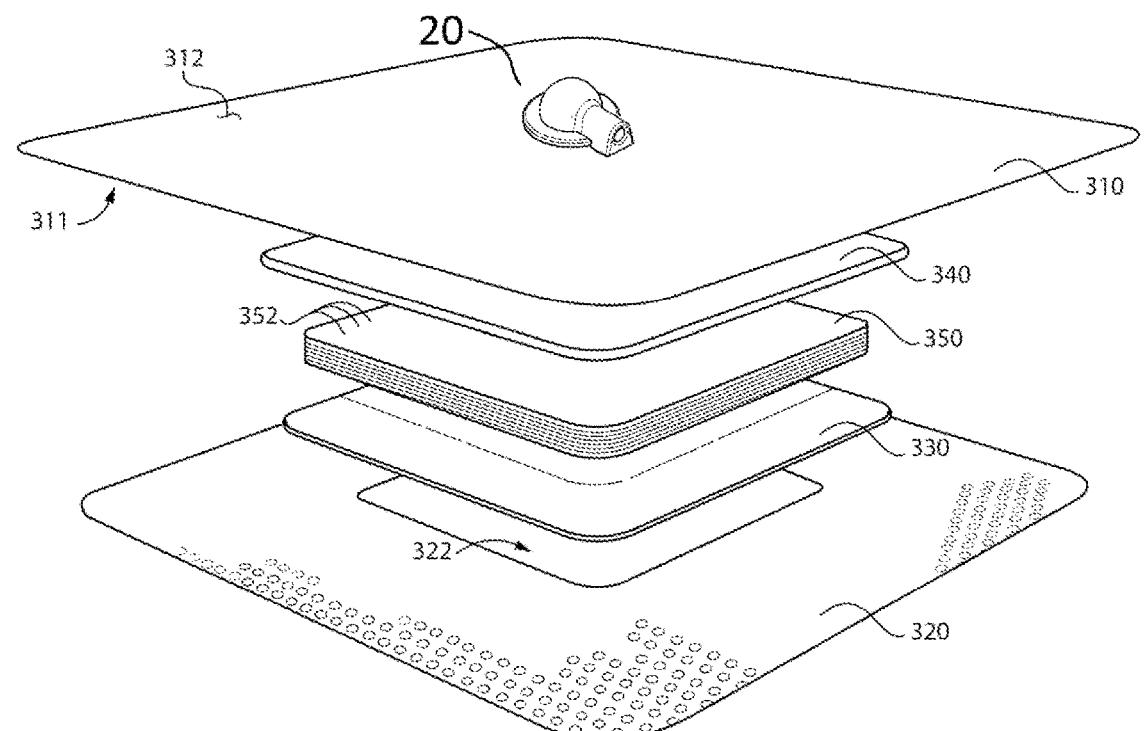
FIG. 6 is an exploded view of the embodiment of the wound dressing of FIG. 3 configured for use with a pressure gradient wound therapy apparatus

FIG. 6 shows the wound dressing 1 of FIGS. 3-5 configured for use with a pressure gradient wound therapy system. Here, a user has applied a port 20 of a second embodiment according to FIG. 7c to the cover layer 310.

Figure 7C:
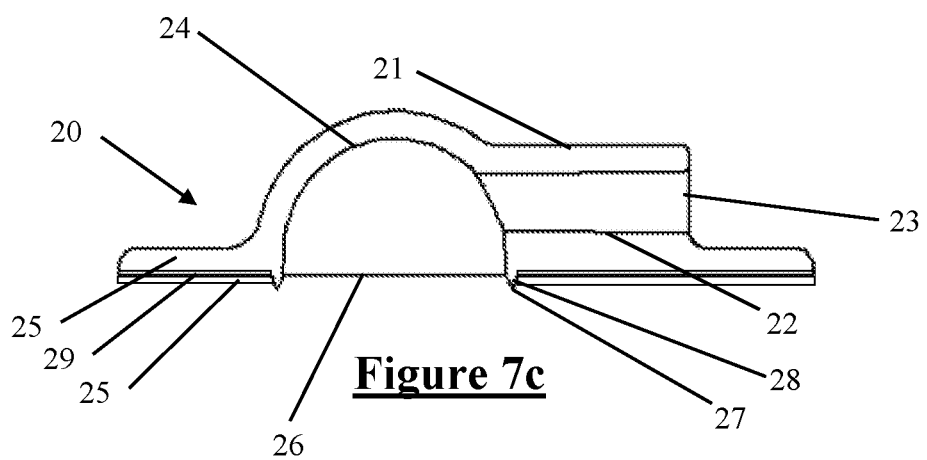
FIG. 7c is a cross section through a port of another embodiment.
Figure 8A:
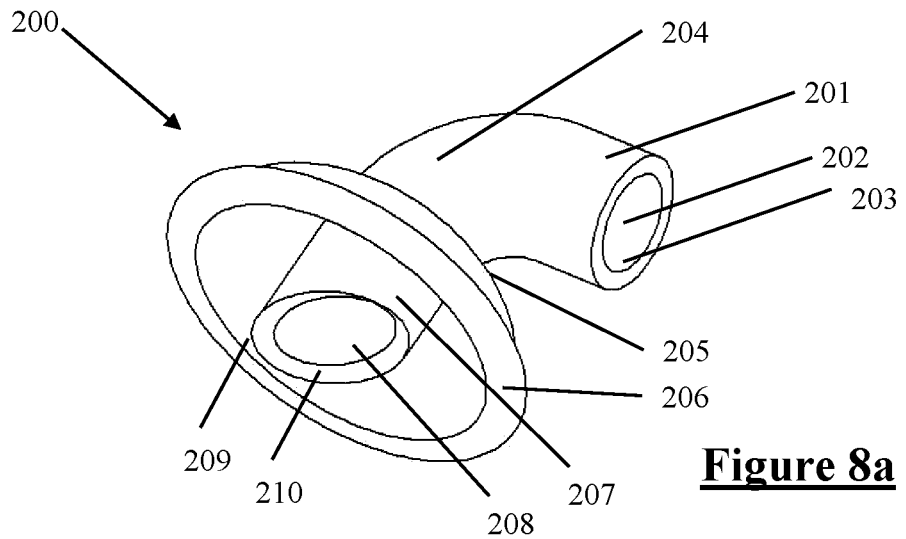
FIG. 8a is an underside perspective view of a port of another embodiment.
Figure 8B:
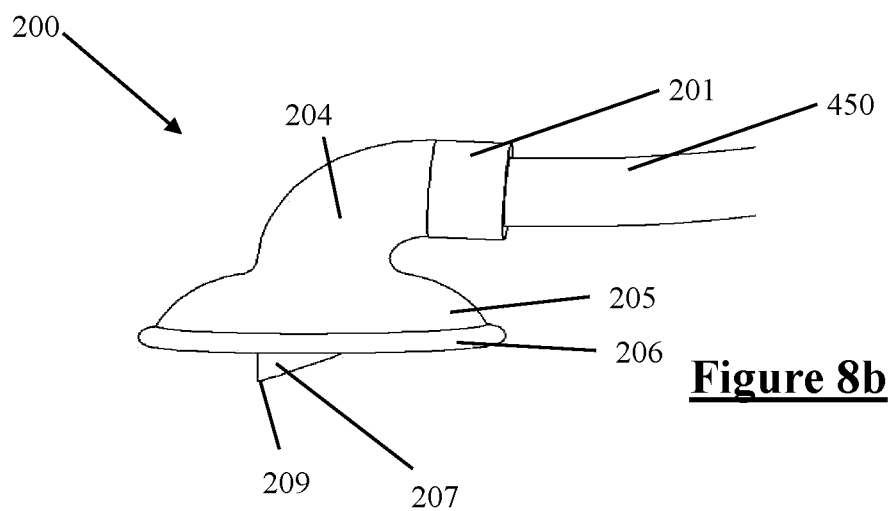
FIG. 8b is a cross section through the port of FIG. 8a connected to tubing.

The port 20 of FIG. 7c is identical to that of FIG. 7b in most respects and like numerals are used to identify like parts. The difference lies in the provision of a layer of adhesive 29 on the underside of the base plate 25 and a removable release layer 30 on the adhesive 29 and the fact that (although it cannot be seen from the figures) the cutting edge 27 is not a complete circle, but only defines a portion of a circle, e.g. 300 degrees.

To apply the port and simultaneously cut the aperture whilst attaching the port to the cover layer of the wound dressing the user removes the release layer 30 exposing the adhesive 29. Then the user arranges the base of the port 20 on the covering layer 310 of the dressing 300 in the region of the indicia 314.

The user then presses down on the upper surface of the port 20. This pushes the cutting edge 27 into and through the covering layer 310. Continued pressing ensures that the cutting edge extends right through the covering layer 310 and slightly into the pressure distribution layer 340, but not into the layers beneath, whilst simultaneously adhering the port 20 to the wound dressing 300.

Since the port is attached to the wound dressing 300 at the same time as the aperture is cut, and since only 300 degrees of the circle is cut, the "chad" will remain "hanging", attached at the edge of the opening, forming a door, which will be opened by the application of negative pressure applied via the second aperture 26 in the port 20 through the conduit 22 and chamber 24.

As such, whilst the region of the covering layer 310 within the peripheral adhesive border defined by the layer 320 is now interrupted by the aperture, which forms an opening, it is simultaneously covered, by the port 20.

A third embodiment of a port 200 is shown in FIGS. 8a to 9b. The port 200 of the third embodiment is also specially configured, not only to carry out its primary function associated with prior art ports (i.e. to connect the wound dressing to a source of negative pressure), but also to pierce the covering layer of a wound dressing, whilst not cutting too deeply into the dressing. Of course, the port 200 may be provided in a sterile package and as part of a kit, as discussed in more detail below, with reference to FIG. 11.

Focusing initially on the primary and standard function of the port, 200, the port 200 (that of connecting a non-atmospheric pressure source to a wound dressing), the port 200 can be seen to include a short, generally tubular, connector part 201 with a conduit 202 extending from a first aperture 203 configured to connect to a non-atmospheric pressure source, in the form of tubing. The connection being made by a simple push-fit of the tubing into the aperture, so that it is held in a resistance fit in the conduit 202.

The conduit 202 in this third embodiment extends through the port, with the short generally tubular connector part 201, merging into a curved, intermediate part 204, which has an angle of approximately 90 degrees, such that one end of the intermediate part 204 is substantially perpendicular to the other.

Extending radially outwardly from the end of the curved intermediate part 204 distal from the tubular connector part 201 is a skirt 205. The skirt 205 forms a housing; it is dome-shaped and terminates in a rim or lip 206 which serves as a base of the port 200 and constitutes one part of a wound dressing contact surface of the port 200. The rim 206 is provided with an adhesive underside to adhere to a wound dressing 1.

The adhesive underside of the wound dressing contact surface may of course be covered by a release liner (not shown). The rim 206 of the skirt 205 is orthogonal to the first aperture 203 of the connector part 201 which receives the tubing, so that in use, with the rim 206 of the skirt 205 adhered to the top of the wound dressing 1, the tubing extends in a direction substantially parallel with the plane of the wound dressing.

Within the skirt 205, the conduit 202 continues from the end of the intermediate part 204 (downwardly in use) and is defined by a tubular piercing part 207, which is the piercing means of this second embodiment. The tubular piercing part 207 includes a second aperture 208 which also contacts (and is in fluid communication with) the wound dressing in use, and as such constitutes another part of a wound dressing contact surface of the port 200. The conduit 202 extends between the first aperture 203 and the second aperture 208, providing fluid communication between the two apertures 203, 208. As such the port is configured to allow fluid communication with the wound dressing via the first aperture 203 and second aperture 206, which is orthogonal thereto. Of course, various alternative shapes and sizes of port may be determined by those skilled in the art.

The end of the tubular piercing part 207 constitutes a cutting edge. The end is formed at an oblique angle, so as to create a piercing tip 209 (in as similar fashion to the well-known piercing drinking straws provided with children's drinks cartons, as described in the prior art section of GB2247227A and the tips of needles). Moreover, the end of the tubular piercing part 207 is provided with an optional internal bevel 210 to further sharpen the cutting edge.

As with the other embodiments, the piercing means is configured to pierce the cover layer of a wound dressing as the wound dressing contact surface of the port 20 is applied to the wound dressing. In this embodiment too, the cutting edge of the piercing part 207 is formed integrally with the port, but naturally, again, a separate blade could be attached at the end of, or could even form, the tubular piercing part 207.

Again, the piercing means of this embodiment is intended to cut a circular aperture, and therefore has a curved cutting edge.

As noted above, it is important that this predetermined extended distance by which the cutting edge extends from the underside of the base of the port is carefully controlled, so as to control how far into the wound dressing the cutting edge extends.

As such, in this an example, the predetermined extended distance by which the piercing tip 209 extends beyond the plane of the underside of the skirt 205, which defines the wound dressing contact surface, may be greater than 0.2 mm; greater than 0.5 mm; greater than 1 mm; greater than 1.5 mm; greater than 2 mm; greater than 2.5 mm; greater than 3 mm or greater than 3.5 mm. The predetermined distance may be less than 10 mm; less than 7 mm; less than 5 mm; less than 4 mm; less than 3.5 mm; less than 3 mm; less than 2.5 mm; or less than 1 mm. For example, the predetermined distance may be between 0.5 mm and 2.5 mm, such as between 1 mm and 2 mm, for example about 1.5 mm.

Figure 9A:
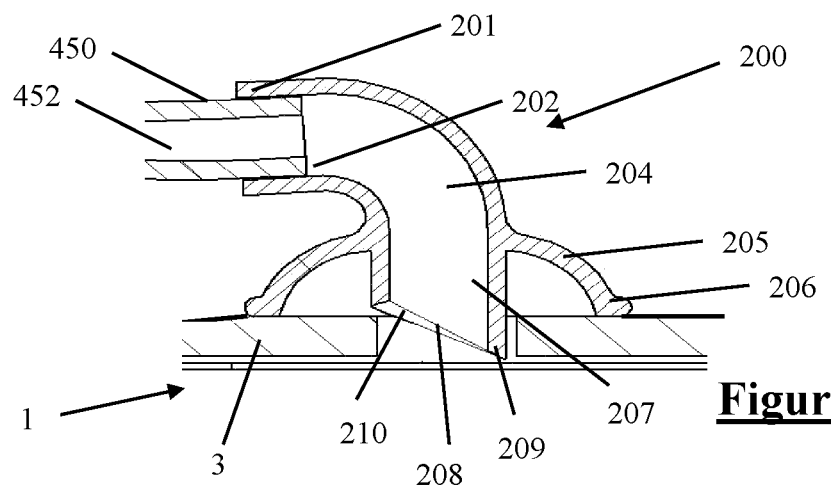
FIG. 9a is a cross section through the port of FIGS. 8a and 8b applied to a wound dressing.
Figure 9B:
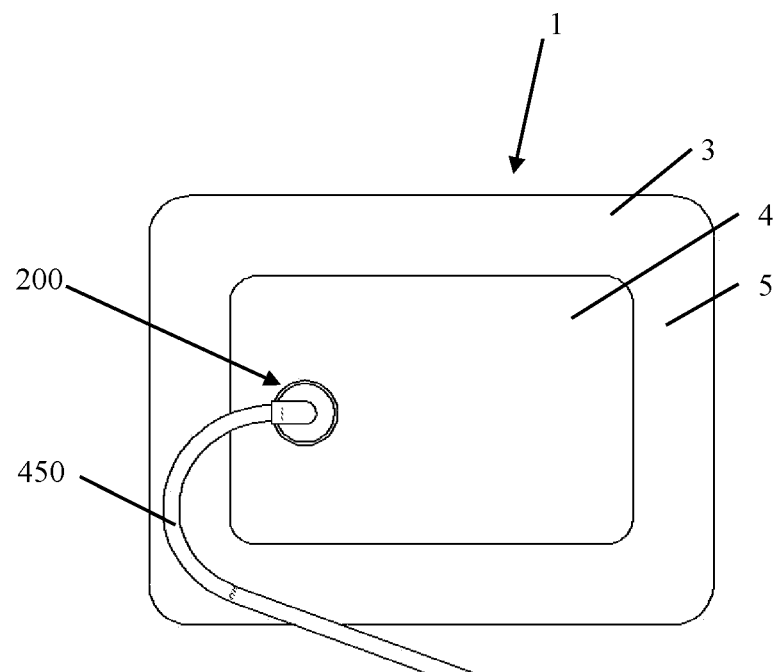
FIG. 9b is a plan view of the wound dressing of FIG. 9a with the port applied.

To cut a circular aperture in the wound dressing, as shown in FIG. 9*a*, the port is pushed onto the wound dressing 1, such that the piercing tip cuts though the covering layer 3; the skirt 205 acts as a stop preventing over-insertion. The port 200 is then twisted so as to cut a circular aperture in the cover layer 3, and the release liner (not shown) removed from the underside of the skirt and the port 200 adhered in place, with the aperture 208 at the bottom of the conduit, coaxial with the aperture cut in the covering layer 3 to draw fluid through it. The "chad" can either be removed by hand, or sucked out through the conduit in use.

As an alternative to twisting, the port 200 can simply be pressed onto the wound dressing 1, cutting an aperture in the cover layer, but potentially not cutting a "chad" out, rather leaving it "hanging". This need not cause a problem as fluid can flow past the hanging chad.

Once again it will be understood that as the port 200 is applied to the dressing it cuts an aperture therein. The aperture may be cut at the same time as the port is attached, e.g. as it is adhered to the wound dressing. Obviously in that case, the step of removal of a chad by would be impossible, but it could simply be sucked out by a source of negative pressure.

A fourth embodiment of a port 2000 is shown in FIGS. 12*a* to 12*e*. The port 2000 of the third embodiment is also specially configured, not only to carry out its primary function associated with prior art ports (i.e. to connect the wound dressing to a source of negative pressure), but also to pierce the covering layer of a wound dressing, whilst not cutting too deeply into the dressing. Of course, the port 2000 may be provided in a sterile package and as part of a kit, as discussed in more detail below, with reference to FIG. 11.

Focusing initially on the primary and standard function of the port 2000, (that of connecting a non-atmospheric pressure source to a wound dressing), the port 2000 can be seen to include a short, generally tubular, connector part 2001 with a conduit 2002 extending from a first aperture 2003 configured to connect to a non-atmospheric pressure source, in the form of tubing. The connection is made by a simple push-fit of the tubing into the aperture 2003, so that it is held in a resistance fit in the conduit 2002.

The conduit 2002 in this fourth embodiment opens into the side of a large generally shallow cylindrical chamber 2004, defined primarily by a shell 2050 having the shape of a shallow, brimmed hat. The brimmed-hat shaped shell is formed of a resiliently flexible material, such as sort plastic, so that the top forms an actuator, which can be pushed downwards and will resile upwards.

The brimmed hat shaped shell 2050 sits on an annular base plate 2005. The annular base plate 2005 has the same outer outline as the brim of the shell 2050, but a smaller opening than that at the base of the shallow cylindrical chamber 2004. The annular base pate 2005 is formed of a hard plastic material and thus provides rigidity. The underside of the base plate 2005 and the base of the dome provides a wound dressing contact surface at the base of the port 2000. The base plate 2005 and shell 2050 together form a housing. The base of the hemispherical chamber is open, but on account of its smaller inner diameter, the opening in the base plate 2005 defines a second aperture 2006, which is provided in the wound dressing contact surface and is in fluid communication with the first aperture via the shallow cylindrical chamber 2004 and conduit 2002. As such the port is configured to allow fluid communication with the wound dressing via the first aperture 2003 and second aperture 2006, which is orthogonal thereto. Of course, various alternative shapes and sizes of port may be determined by those skilled in the art.

The port 2000 of this embodiment also includes a piercing means configured to pierce the cover layer of a wound dressing as the wound dressing contact surface of the port 2000 is applied to the wound dressing. In this embodiment, the piercing means is more sophisticated and the form of a cutting edge 2007 formed integrally with a flexure disc spring 2100 shown separately in FIGS. 12*c*, 12*d* and 12*e*. The cutting edge 2007 is provided at the end of a downwardly depending annular projection 2008 extending from the disc spring 2100 and configured to extend through the aperture 2006. The annular projection 2008 is stepped, such that it is provided with a shoulder 2200, the shoulder having a larger diameter than the aperture 2006 in the base plate 2005 and therefore defining the extent to which the blade 2007 can extend into the wound dressing.

The piercing means of this embodiment is once again intended to cut a circular aperture, and therefore has a curved cutting edge 2007, which defines a circle (to allow a circular aperture to be cut into the wound dressing, to match the shape the aperture 2006). In this embodiment the cutting edge 2007 is serrated. Obviously the blade need not be serrated (as in the other embodiments).

The cutting edge 2007 and the disc spring 2100 from which it depends are, advantageously, made of metal. The outer peripheral edge 2300 of the disc spring is fitted into a corresponding circular groove in the shell 2050. The groove extends radially outwardly into the sidewall of the shell, near its top. As such, the top of the shell is an actuator, acting as a button, and pressing downwardly on the top of the resilient shell pushes the centre of the spring downwards. The cutting edge 2007 extends downwardly near the centre of the disc spring 2100, and as such it moves downward when the button is pressed.

It is important that this predetermined extended distance by which the cutting edge 2007 extends from the underside of the base plate 2005 is carefully controlled, so as to control how far into the wound dressing the cutting edge 2007 extends.

In particular, it can be provided that the cutting edge 2007 cuts right through the covering layer 3 of a wound dressing, but not into any layer beneath. Alternatively, for example, where the port 2000 is for use in a dressing with a pressure distribution layer sandwiched between a covering layer and an absorbent layer (as discussed below with reference to FIGS. 3-6), the cutting edge 2007 can be arranged to extend through the covering layer 310, to extend into the pressure distribution layer 340 and not to extend into the absorbent layer(s) 350 (or the wound contact layer 330).

This means that fluid can pass through the aperture cut into the covering layer, whilst not cutting too deeply into the body of the dressing, so as to reduce damage to internal parts of the dressing, such as a pressure distribution layer, or an absorbent layer.

The extent to which the cutting edge extends is defined by the shoulder 2200 and as an example, the predetermined extended distance may be greater than 0.2 mm; greater than 0.5 mm; greater than 1 mm; greater than 1.5 mm; greater than 2 mm; greater than 2.5 mm; greater than 3 mm or greater than 3.5 mm. The predetermined distance may be less than 10 mm; less than 7 mm; less than 5 mm; less than 4 mm; less than 3.5 mm; less than 3 mm; less than 2.5 mm; or less than 1 mm. For example, the predetermined distance may be between 0.5 mm and 2.5 mm, such as between 1 mm and 2 mm, for example about 1.5 mm.

The extent to which the cutting edge retracts is similarly carefully controlled and as an example, the predetermined retracted distance may be greater than 0.2 mm; greater than 0.5 mm; greater than 1 mm; greater than 1.5 mm; greater than 2 mm; greater than 2.5 mm; greater than 3 mm or greater than 3.5 mm. The predetermined distance may be less than 10 mm; less than 7 mm; less than 5 mm; less than 4 mm; less than 3.5 mm; less than 3 mm; less than 2.5 mm; or less than 1 mm. For example, the predetermined distance may be between 0.5 mm and 2.5 mm, such as between 1 mm and 2 mm, for example about 1.5 mm.

If the cutting edge is sharp enough, it can be simply pushed onto the wound dressing to cut the aperture 6 as shown in FIG. 2. The retraction of the blade allows plenty of space beneath it for fluid to be sucked into the chamber 2004 and out through the conduit 2002. As such, the "chad" need not necessarily be removed, and the port 2000 can be adhered around the aperture 6 in the wound dressing at the same time that it cuts the hole. Alternatively, to improve cutting, the port 2000 could be twisted before adhering it to the wound dressing. Preferably the underside of the base plate 2005 is provided with an adhesive (not shown) and a release liner (not shown), for example a double-sided adhesive tape.

The adhesive underside of the wound dressing contact surface may of course be covered by a release liner (not shown). The rim 206 of the skirt 205 is orthogonal to the first aperture 203 of the connector part 201 which receives the tubing, so that in use, with the rim 206 of the skirt 205 adhered to the top of the wound dressing 1, the tubing extends in a direction substantially parallel with the plane of the wound dressing.

Figure 10:
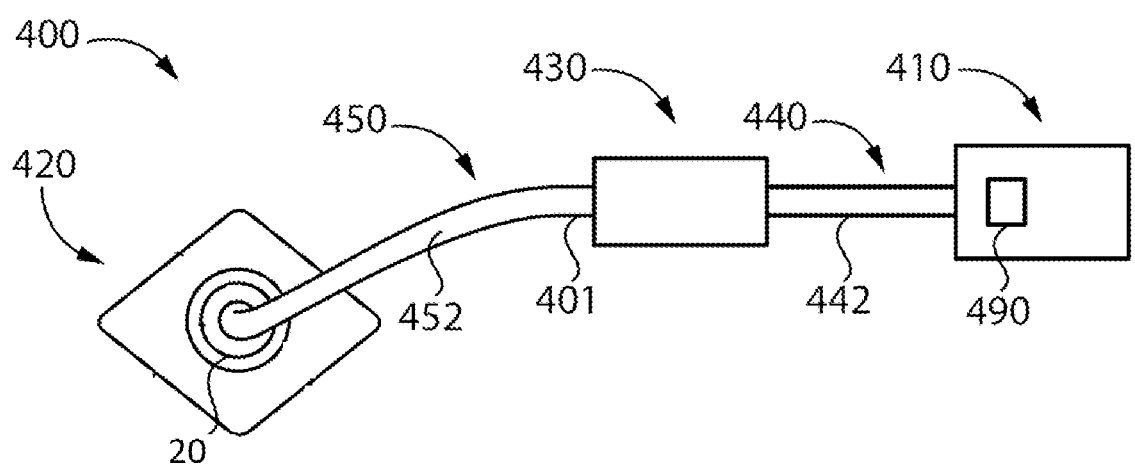
FIG. 10 is a schematic representation of a wound exudate management system according to certain embodiments.

With additional reference to FIG. 10, illustrated therein is a pressure gradient wound therapy system 400 according to certain embodiments. The pressure gradient wound therapy system 400 comprises a pump 410 for generating negative pressure, a wound dressing 420 (which may be the wound dressing 1 or 300 described above) for covering and protecting a wound, an inline filter 430, a first pressure tube 440 having a first interior lumen 442, a second pressure tube 450 having a second interior lumen 452, and connected to a port 20/200/2000. The first pressure tube 440 is disposed between the pump 410 and the inline filter 430. The second pressure tube 450 is disposed between the inline filter 430 and the port 20/200/2000. The port 20/200/2000 is disposed between the second pressure tube 450 and the wound dressing 420 such that the pump 410 and the wound dressing 420 are in fluid communication via the interior lumens 442, 452.

The port 20/200/2000 is preferably provided in a kit and most preferably arranged in the kit within a sterile package. As illustrated schematically in FIG. 11, the kits can comprise a port 20/200/2000 within a sterile package 28 and at least one of the following items, all of which are included in this exemplary kit:

(a) packaging 500 indicating that the port is configured to pierce a covering layer of a wound dressing to produce an aperture therein and thereby configure the wound dressing for use in a pressure gradient wound therapy. In this example the packaging is a cardboard box, printed with instructions for use.

(b) instructions instructing a user as to how to use the port to configure a wound dressing for use in a pressure gradient wound therapy system. In this example, the instructions are printed on a leaflet 502 included in the box.

(c) one or more selectively configurable wound dressings 1, 300, 420, the wound dressings 1, 300, 420 being configurable for use in a pressure gradient wound therapy system and without a pressure gradient wound therapy system. In this embodiment, a plurality of such wound dressings 1, 300, 420 are provided, each in individual sterile packages.

(d) a source of non-atmospheric pressure. In this embodiment, the source of non-atmospheric pressure is the pump 410.

(e) tubing for connection between a wound dressing and a source of non-atmospheric pressure. In this embodiment tubing 450 described above is included.

For use where it is envisioned that a wound will initially require treatment with a pressure gradient wound therapy system, the kit may comprise a port 20/200/2000 and one or more of items d and e, for example both of items, d, and e, and optionally items a and/or b and/or c as well. As such, the user can be provided with all the equipment required to use the wound dressings 1/300/420 with a pressure gradient wound therapy system.

In order to use such a kit, the user (e.g. a patient or HCP) can cut an aperture in a dressing 1/30/420, optionally in the region of indicia, using the piercing means of the port 20/200/2000; attach the port 20/200/2000 thereto, around the aperture, and in fluid communication therewith; attach one end of the tubing 450 to the port 20/200/2000 and the other to the pump 410 and run the pump 410 to provide non-atmospheric (e.g. negative) pressure to the wound.

Then, if/when the pressure gradient therapy is no longer necessary, the user can use up any remaining wound dressings 1/300/420 without the pressure gradient wound therapy system, by applying them to the wound without cutting an aperture in the dressings 1/300/420, so as to maintain a sealed environment around the wound.

On the other hand, for use where it is envisioned that a wound does not initially require treatment with a pressure gradient wound therapy system (and most preferably where it is envisioned that a wound does not require treatment with a pressure gradient wound therapy system, but it is considered that there is a risk that the wound will not heal well without a pressure gradient so in future, pressure gradient wound therapy might be useful), the kit may comprise the port 20/200/2000, one or preferably a plurality of the dressings of item c, and preferably one or both of items a and b. As such, the user has the dressings which can be used without a pressure gradient wound therapy system and can simply apply a dressing 1/300/420 to the wound in the configuration for use without a pressure gradient wound therapy system. Thus the user simply remove the release layer and apply the dressing to the wound without cutting an aperture in the region of the indicia 2, 314, so that the cover layer is uninterrupted and closed within the adhesive border, and the is wound sealed against bacteria/microbes.

Then, should it be determined that the wound would benefit from pressure gradient therapy (e.g. negative pressure), the user can follow the instructions from the packaging/instructions (where included), and cut a hole in the covering layer 3/310 in the region of the indicia 2/314 using the piercing means of the port 20/200/2000 and apply a pressure gradient wound therapy system as outlined above (sourced for example from another kit), without having to first remove the dressing 1/300/420 (which can present an opportunity for infection).

For use where it is determined after the event that NPWT would be useful the kit could include a port and one or more of items d, and e, for example both of items, d, and e, and optionally items a and/or b and/or c as well would be useful. As such, the user can be provided with all the equipment required to convert a wound dressing 1/300/420 in-situ for use with a pressure gradient wound therapy system.

In order to use such a kit, the user (e.g. a patient or HCP) can cut an aperture in a dressing 1/30/420, optionally in the region of indica, using the piercing means of the port 20/200/2000; attach the port 20/200/2000 thereto, around the aperture, and in fluid communication therewith; attach one end of the tubing 450 to the port 20/200/2000 and the other to the pump 410 and run the pump 410 to provide non-atmospheric (e.g. negative) pressure to the wound.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Each of the documents referred to above is incorporated herein by reference. Except in Examples, or where otherwise explicitly indicated, all numerical quantities in this description specifying amounts of materials, device dimension, and the like, are to be understood as modified by the word "about."

Unless otherwise indicated, each chemical or composition referred to herein should be interpreted as being a commercial grade material which may contain the isomers, by-products, derivatives, and other such materials which are normally understood to be present in the commercial grade.

The one or more embodiments are described above by way of example only. Many variations are possible without departing from the scope of protection afforded by the appended claims.

The invention claimed is:

1. A port for connecting a non-atmospheric pressure source to a wound dressing, the port comprising:
  a first aperture configured to connect to the non-atmospheric pressure source;
  a wound dressing contact surface, the wound dressing contact surface comprising a second aperture in fluid communication with the first aperture and configured to allow fluid communication with the wound dressing;
  a housing; and
  a piercing means configured to pierce the wound dressing as the wound dressing contact surface of the port is applied to the wound dressing,
  wherein the piercing means extends from the housing beyond the wound dressing contact surface; and
  wherein the piercing means is configured to be retractable into the housing.

2. A port according to claim 1 wherein the piercing means has a curved cutting edge.

3. A port according to claim 2 wherein the piercing means has a circular cutting edge.

4. A port according to claim 1, wherein the piercing means is fixed in position extending from the housing.

5. A port according to claim 1, wherein the piercing means is movable to a retracted position when negative pressure is applied to the first aperture in the port.

6. A port according to claim 1, wherein the piercing means is biased towards a retracted position.

7. A port according to claim 1, wherein the wound dressing contact surface comprises a base; and
  wherein the base is provided with an adhesive underside for connection to the dressing.

8. A port according to claim 1, further comprising:
  a connector part comprising the first aperture configured to connect to the non-atmospheric pressure source; and
  a base plate comprising the wound dressing contact surface;
  wherein the connector part and the base plate are separable.

9. A port according to claim 1, wherein the first aperture is orthogonal to the second aperture.

10. A port according to claim 1, wherein the wound dressing contact surface is the lowest surface of the housing.

11. A packaged kit of parts for use with a configurable wound dressing, the wound dressing being configurable for use in a pressure gradient wound therapy system and without a pressure gradient wound therapy system; the kit comprising a port according to claim 1 and at least one of:
  (a) packaging indicating that the port is configured to pierce a wound to produce an aperture therein and thereby configure the wound dressing for use in a pressure gradient wound therapy;
  (b) instructions instructing a user as to how to use the port to configure a wound dressing for use in a pressure gradient wound therapy system;
  (c) one or more configurable wound dressings, the wound dressings being configurable for use in a pressure gradient wound therapy system and without a pressure gradient wound therapy system;
  (d) a source of non-atmospheric pressure; or
  (e) tubing for connection between a wound dressing and a source of non-atmospheric pressure;
  the kit being arranged within a sealed package.

12. A packaged kit of parts according to claim 11 comprising at least:
  (a) packaging indicating that the port is configured to pierce a covering layer of a wound dressing to produce an aperture therein and thereby configure the wound dressing for use in a pressure gradient wound therapy; or (b) instructions instructing a user as to how to use the port to configure a wound dressing for use in a pressure gradient wound therapy system.

13. A packaged kit of parts according to claim 11 comprising at least (c) one or more configurable wound dressings, the wound dressings being configurable for use in a pressure gradient wound therapy system and without a pressure gradient wound therapy system and comprising a covering layer and at least two further layers, the at least two further layers comprising a first layer adjacent the covering layer and a second layer separated from the covering layer by the layer;

wherein the cutting edge is arranged to extend through the covering layer, to extend into the first layer and not to extend into the second layer.

14. A packaged kit of parts according to claim 13 wherein the wound dressing is a one-piece dressing, and wherein the covering layer and the first and second layers of the wound dressing are provided as an integral item.

15. A packaged kit of parts according to claim 13, wherein the covering layer comprises an indicium, the indicium denoting a suitable position in the covering layer to create an aperture to provide fluid communication between the pressure distribution layer and a source of non-atmospheric pressure.

16. A packaged kit of parts according to claim 11 comprising at least:

(d) a source of non-atmospheric pressure, wherein the source of non-atmospheric pressure is a pump, which provides a source of negative pressure; or (e) tubing for connection between a wound dressing and a source of non-atmospheric pressure, wherein the tubing is formed from a resilient flexible plastics material.

17. A pressure gradient wound therapy apparatus, comprising the kit of claim 11, the kit including each of items (a) to (e).

18. A port for connecting a non-atmospheric pressure source to a wound dressing, the port comprising:

a first aperture configured to connect to the non-atmospheric pressure source;

a wound dressing contact surface, the wound dressing contact surface comprising a second aperture in fluid communication with the first aperture and configured to allow fluid communication with the wound dressing;

a housing; and a piercing means configured to pierce the wound dressing as the wound dressing contact surface of the port is applied to the wound dressing;

wherein the piercing means extends from the housing beyond the wound dressing contact surface; and wherein the housing comprises an actuator and actuation of the actuator moves the piercing means into an extended position.

\* \* \* \* \*